US012575797B2

(12) United States Patent
Olsen et al.

(10) Patent No.: US 12,575,797 B2
(45) Date of Patent: Mar. 17, 2026

(54) BLOOD GLUCOSE DISEASE MANAGEMENT SYSTEM

(71) Applicant: Cercacor Laboratories, Inc., Irvine, CA (US)

(72) Inventors: Gregory A. Olsen, Lake Forest, CA (US); Sai Kong Frank Lee, Irvine, CA (US); Jesse Chen, Foothill Ranch, CA (US); Hung The Vo, Fountain Valley, CA (US); Kevin Hughes Pauley, Lake Forest, CA (US)

(73) Assignee: Willow Laboratories, Inc., Irvine, CA (US)

( * ) Notice: Subject to any disclaimer, the term of this patent is extended or adjusted under 35 U.S.C. 154(b) by 195 days.

(21) Appl. No.: 17/344,342

(22) Filed: Jun. 10, 2021

(65) Prior Publication Data

US 2021/0386382 A1 Dec. 16, 2021

Related U.S. Application Data

(60) Provisional application No. 63/037,973, filed on Jun. 11, 2020.

(51) Int. Cl.
*A61B 5/00* (2006.01)

(52) U.S. Cl.
CPC ........... *A61B 5/742* (2013.01); *A61B 5/4839* (2013.01); *A61B 5/7275* (2013.01); *A61B 5/7405* (2013.01); *A61B 5/7455* (2013.01); *A61B 5/746* (2013.01)

(58) Field of Classification Search
CPC ..... A61B 5/742; A61B 5/4839; A61B 5/7275; A61B 5/7405; A61B 5/7455; A61B 5/746
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |

(Continued)

OTHER PUBLICATIONS

US 2024/0016391 A1, 01/2024, Lapotko et al. (withdrawn)

*Primary Examiner* — Alex M Valvis
*Assistant Examiner* — Grace L Rozanski
(74) *Attorney, Agent, or Firm* — KNOBBE, MARTENS, OLSON & BEAR, LLP

(57) ABSTRACT

The disease management system can determine a measurement of one or more physiological parameters and can determine a disease event based on the one or more measurements. Furthermore, the disease management system can determine a pose of an individual using a pose sensor. Based on an identification of a disease event and a determination that the pose of the individual corresponds to a first pose, the disease management system can cause at least one of an audible, visual, or vibratory alarm. Based on an identification of a disease event and a determination that the pose of the individual does not correspond to the first pose, the disease management system can cause administration of a medication to the individual.

20 Claims, 12 Drawing Sheets

(56) References Cited

U.S. PATENT DOCUMENTS

| | | |
|---|---|---|
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |

(56)                     References Cited

U.S. PATENT DOCUMENTS

| | | | |
|---|---|---|---|
| D621,516 | S | 8/2010 | Kiani et al. |
| 7,791,155 | B2 | 9/2010 | Diab |
| RE41,912 | E | 11/2010 | Parker |
| 7,880,626 | B2 | 2/2011 | Al-Ali et al. |
| 7,909,772 | B2 | 3/2011 | Popov et al. |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,941,199 | B2 | 5/2011 | Kiani |
| 7,957,780 | B2 | 6/2011 | Lamego et al. |
| 7,962,188 | B2 | 6/2011 | Kiani et al. |
| 7,976,472 | B2 | 7/2011 | Kiani |
| 7,990,382 | B2 | 8/2011 | Kiani |
| 8,008,088 | B2 | 8/2011 | Bellott et al. |
| RE42,753 | E | 9/2011 | Kiani-Azarbayjany et al. |
| 8,028,701 | B2 | 10/2011 | Al-Ali et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,130,105 | B2 | 3/2012 | Al-Ali et al. |
| 8,182,443 | B1 | 5/2012 | Kiani |
| 8,190,223 | B2 | 5/2012 | Al-Ali et al. |
| 8,203,438 | B2 | 6/2012 | Kiani et al. |
| 8,203,704 | B2 | 6/2012 | Merritt et al. |
| 8,219,172 | B2 | 7/2012 | Schurman et al. |
| 8,224,411 | B2 | 7/2012 | Al-Ali et al. |
| 8,229,532 | B2 | 7/2012 | Davis |
| 8,233,955 | B2 | 7/2012 | Al-Ali et al. |
| 8,255,026 | B1 | 8/2012 | Al-Ali |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,315,683 | B2 | 11/2012 | Al-Ali et al. |
| RE43,860 | E | 12/2012 | Parker |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,374,665 | B2 | 2/2013 | Lamego |
| 8,388,353 | B2 | 3/2013 | Kiani et al. |
| 8,401,602 | B2 | 3/2013 | Kiani |
| 8,414,499 | B2 | 4/2013 | Al-Ali et al. |
| 8,418,524 | B2 | 4/2013 | Al-Ali |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,707 | B2 | 6/2013 | Kiani |
| 8,471,713 | B2 | 6/2013 | Poeze et al. |
| 8,473,020 | B2 | 6/2013 | Kiani et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| D692,145 | S | 10/2013 | Al-Ali et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,579,879 | B2 | 11/2013 | Palerm et al. |
| 8,584,345 | B2 | 11/2013 | Al-Ali et al. |
| 8,588,880 | B2 | 11/2013 | Abdul-Hafiz et al. |
| 8,630,691 | B2 | 1/2014 | Lamego et al. |
| 8,641,631 | B2 | 2/2014 | Sierra et al. |
| 8,652,060 | B2 | 2/2014 | Al-Ali |
| 8,666,468 | B1 | 3/2014 | Al-Ali |
| 8,670,811 | B2 | 3/2014 | O'Reilly |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,702,627 | B2 | 4/2014 | Telfort et al. |
| 8,712,494 | B1 | 4/2014 | MacNeish, III et al. |
| 8,715,206 | B2 | 5/2014 | Telfort et al. |
| 8,723,677 | B1 | 5/2014 | Kiani |
| 8,740,792 | B1 | 6/2014 | Kiani et al. |
| 8,755,535 | B2 | 6/2014 | Telfort et al. |
| 8,755,872 | B1 | 6/2014 | Marinow |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,781,544 | B2 | 7/2014 | Al-Ali et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,840,549 | B2 | 9/2014 | Al-Ali et al. |
| 8,852,094 | B2 | 10/2014 | Al-Ali et al. |
| 8,852,994 | B2 | 10/2014 | Wojtczuk et al. |
| 8,897,847 | B2 | 11/2014 | Al-Ali |
| 8,911,377 | B2 | 12/2014 | Al-Ali |
| 8,989,831 | B2 | 3/2015 | Al-Ali et al. |
| 8,998,809 | B2 | 4/2015 | Kiani |
| 9,066,666 | B2 | 6/2015 | Kiani |
| 9,066,680 | B1 | 6/2015 | Al-Ali et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,131,881 | B2 | 9/2015 | Diab et al. |
| 9,138,180 | B1 | 9/2015 | Coverston et al. |
| 9,153,112 | B1 | 10/2015 | Kiani et al. |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,095 | B1 | 12/2015 | Al-Ali |
| 9,218,454 | B2 | 12/2015 | Kiani et al. |
| 9,245,668 | B1 | 1/2016 | Vo et al. |
| 9,267,572 | B2 | 2/2016 | Barker et al. |
| 9,277,880 | B2 | 3/2016 | Poeze et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,392,945 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,474,474 | B2 | 10/2016 | Lamego et al. |
| 9,480,435 | B2 | 11/2016 | Olsen |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,560,996 | B2 | 2/2017 | Kiani |
| 9,579,039 | B2 | 2/2017 | Jansen et al. |
| 9,622,692 | B2 | 4/2017 | Lamego et al. |
| D788,312 | S | 5/2017 | Al-Ali et al. |
| 9,649,054 | B2 | 5/2017 | Lamego et al. |
| 9,697,928 | B2 | 7/2017 | Al-Ali et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,749,232 | B2 | 8/2017 | Sampath et al. |
| 9,750,442 | B2 | 9/2017 | Olsen |
| 9,750,461 | B1 | 9/2017 | Telfort |
| 9,775,545 | B2 | 10/2017 | Al-Ali et al. |
| 9,778,079 | B1 | 10/2017 | Al-Ali et al. |
| 9,782,077 | B2 | 10/2017 | Lamego et al. |
| 9,787,568 | B2 | 10/2017 | Lamego et al. |
| 9,808,188 | B1 | 11/2017 | Perea et al. |
| 9,839,379 | B2 | 12/2017 | Al-Ali et al. |
| 9,839,381 | B1 | 12/2017 | Weber et al. |
| 9,847,749 | B2 | 12/2017 | Kiani et al. |
| 9,848,800 | B1 | 12/2017 | Lee et al. |
| 9,861,298 | B2 | 1/2018 | Eckerbom et al. |
| 9,861,305 | B1 | 1/2018 | Weber et al. |
| 9,877,650 | B2 | 1/2018 | Muhsin et al. |
| 9,891,079 | B2 | 2/2018 | Dalvi |
| 9,924,897 | B1 | 3/2018 | Abdul-Hafiz |
| 9,936,917 | B2 | 4/2018 | Poeze et al. |
| 9,955,937 | B2 | 5/2018 | Telfort |
| 9,965,946 | B2 | 5/2018 | Al-Ali et al. |
| D820,865 | S | 6/2018 | Muhsin et al. |
| 9,986,952 | B2 | 6/2018 | Dalvi et al. |

(56) References Cited

U.S. PATENT DOCUMENTS

| | | | |
|---|---|---|---|
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| 11,040,141 B2 | 6/2021 | El-Khatib et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |

(56) References Cited

U.S. PATENT DOCUMENTS

| | | |
|---|---|---|
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,061,585 S | 2/2025 | Indorf |
| D1,063,893 S | 2/2025 | DeJong et al. |
| 12,220,207 B2 | 2/2025 | Telfort et al. |
| 12,235,941 B2 | 2/2025 | Kiani et al. |
| 12,236,767 B2 | 2/2025 | Muhsin |
| D1,066,244 S | 3/2025 | Lim et al. |
| D1,066,672 S | 3/2025 | Al-Ali et al. |
| D1,068,656 S | 4/2025 | Trevisan et al. |
| D1,071,195 S | 4/2025 | Seung |
| D1,072,836 S | 4/2025 | Indorf |
| D1,072,837 S | 4/2025 | Ahmed et al. |
| 12,272,445 B1 | 4/2025 | Kiani |
| D1,078,689 S | 6/2025 | Hwang |
| D1,079,020 S | 6/2025 | Hwang |
| 12,336,796 B2 | 6/2025 | Al-Ali |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0004672 A1* | 1/2008 | Dalal .................. A61N 1/36135 |
| | | 607/2 |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0063438 A1* | 3/2010 | Bengtsson .......... A61M 5/1723 |
| | | 340/691.4 |
| 2010/0094110 A1* | 4/2010 | Heller .................. A61B 5/4848 |
| | | 600/345 |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0172927 A1* | 7/2011 | Sahasrabudhe ...... A61B 5/7282 |
| | | 702/19 |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0296178 A1 | 11/2012 | Lamego et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0367173 A1 | 12/2016 | Dalvi et al. |
| 2017/0024748 A1 | 1/2017 | Haider |
| 2017/0028196 A1* | 2/2017 | Stopperan .......... A61N 1/36021 |
| 2017/0156662 A1* | 6/2017 | Goodall ................ A61N 2/002 |
| 2017/0173632 A1 | 6/2017 | Al-Ali |
| 2017/0181645 A1* | 6/2017 | Mahalingam .......... G16H 10/60 |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247095 A1* | 8/2018 | Sundaram ............ A61B 5/0215 |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310823 A1 | 11/2018 | Al-Ali et al. |
| 2019/0015023 A1 | 1/2019 | Monfre |
| 2019/0029567 A1* | 1/2019 | Stahmann ............. A61B 5/1116 |
| 2019/0030366 A1* | 1/2019 | Maltz .................. A61B 5/0536 |

(56)                    References Cited

U.S. PATENT DOCUMENTS

| | | |
|---|---|---|
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0286612 A1 * | 9/2020 | Mears .................... G16H 20/60 |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |

* cited by examiner

400

START CALIBRATION

COMMUNICATE INDICATION TO PERFORM FIRST ACTIVITY — 402

RECEIVE SENSOR DATA — 404

IS THE INDIVIDUAL PERFORMING FIRST ACTIVITY? — 406

NO

YES

OBTAIN MEASUREMENT — 408

COMMUNICATE INDICATION TO PERFORM SECOND ACTIVITY — 410

RECEIVE SENSOR DATA — 412

IS THE INDIVIDUAL PERFORMING SECOND ACTIVITY? — 414

NO

YES

OBTAIN MEASUREMENT — 416

DETERMINE BODY VECTOR — 418

BLOOD GLUCOSE DISEASE MANAGEMENT SYSTEM

CROSS REFERENCE TO RELATED APPLICATIONS

This application claims priority benefit to U.S. Provisional Application No. 63/037,973, filed on Jun. 11, 2020, entitled "EMERGENCY GLUCAGON SYSTEM," which is hereby incorporated by reference herein in its entirety.

FIELD OF THE DISCLOSURE

The general field of this disclosure is glucose sensing and disease management systems.

BACKGROUND

Diabetes is a chronic disease that impacts many individuals, both adults and children. The management of diabetes may include the measurement of glucose and administration of a medication, such as insulin or glucagon, to an individual. A closed loop administration system includes both a sensor to take glucose measurements and an administration device which administers the medication to the individual based on the glucose measurements. Closed loop administration systems allow individuals impacted by diabetes to go about daily life with much less worry about their hormones or glucose levels which can vastly improve a diabetic's quality of life.

Continuous glucose monitors (CGMs) measure the body's blood glucose (blood sugar) levels in real-time by sensing the glucose present in tissue fluid. CGMs are often configured to trigger an alarm when the blood sugar is too low (Hypoglycemia) or too high (Hyperglycemia).

SUMMARY

The present disclosure describes example systems, methods, apparatuses, and medical devices for managing one or more disease events. A disease management system can include a physiological sensor configured to physiological data, a pose sensor configured to provide pose information, and one or more processors in communication with the physiological sensor and the pose sensor. The one or more processors can be configured to determine a pose of an individual based at least in part on the pose information, determine a measurement of a physiological parameter based at least in part on the physiological data, and identify a disease event based at least in part on the measurement of the physiological parameter. Based at least in part on the identification of the disease event and a determination that the pose of the individual corresponds to a first pose, the one or more processors are configured to cause at least one of an audible, visual, or vibratory alarm. Based at least in part on the identification of the disease event and a determination that the pose of the individual does not correspond to the first pose, the one or more processors are configured to cause administration of a medication to the individual, wherein the administration of the medication to the individual causes a change in the physiological parameter.

A disease management system can include one or more processors can be configured to, determine a measurement of a physiological parameter, identify a disease event based at least in part on the measurement of the physiological parameter, determine a pose of an individual, output an instruction to changes poses, and cause administration of a medication to the individual based on a determination that the individual changed poses.

A disease management system can include one or more processors can be configured to, determine a measurement of a physiological parameter, identify a disease event based at least in part on the measurement of the physiological parameter, determine a pose of an individual, and cause administration of a medication to the individual based on a determination that the pose is an acceptable pose for receiving the medication.

A disease management system can be configured to provide a technique for managing the hypoglycemic state. The disease management system can automatically administer glucagon to an individual based on one or more measurements of physiological parameters. In this way, the disease management system can reduce a number of false alarms and/or instances of sleep disruption or insomnia, as compared to conventional systems. Further, the disease management system can monitor a pose of the individual and can prevent administration of glucagon to the individual when the individual is lying on his or her back.

The disease management system of any of the preceding paragraphs may also include any combination of the following features described in this paragraph, among others described herein. The physiological data can include blood glucose measurement data. The measurement can include a blood glucose measurement.

The disease management system of any of the preceding paragraphs may also include any combination of the following features described in this paragraph, among others described herein. The one or more processors can be configured to perform a calibration procedure. Performance of the calibration procedure can calibrate the pose of the individual relative to a pose of the disease management system. To perform the calibration procedure, the one or more processors can be configured to obtain a set of pose data from the pose sensor, and calibrate the pose sensor based at least in part on the set of pose data. The set of pose data can correspond to a plurality of activities of the individual. The plurality of activities can include standing, walking, running, sitting up, spinning, lying on back, lying on stomach, lying on side. To perform the calibration procedure, the one or more processors can be configured to obtain first pose information from the pose sensor, obtain second pose information from the pose sensor, and calibrate the pose sensor based at least in part on the first pose information and the first pose information. The first pose information can correspond to a first activity of the user; The second pose information can correspond to a second activity of the user.

The disease management system of any of the preceding paragraphs may also include any combination of the following features described in this paragraph, among others described herein. The first activity can correspond to standing and the second activity can correspond to walking in a straight line. To obtain the first pose information, the one or more processors can be configured to communicate a first instruction indicating for the individual to perform the second activity, determine that the individual is not moving, and responsive to the determination that the individual is not moving, obtain the second pose information. To obtain the second pose information, the one or more processors can be configured to communicate a second instruction indicating for the individual to perform the second activity, determine that the individual is moving, and responsive to the determination that the individual is moving, obtain the second pose information.

The disease management system of any of the preceding paragraphs may also include any combination of the following features described in this paragraph, among others described herein. The medication can include glucagon. The disease event can correspond to Hypoglycemia. The disease event can correspond to blood glucose, and the one or more processors can be configured to identify the disease event by determining that the blood glucose does not satisfy a threshold. The medication can include insulin. The disease event can correspond to Hyperglycemia.

The disease management system of any of the preceding paragraphs may also include any combination of the following features described in this paragraph, among others described herein. The disease management system can be a wearable system configured to by worn by the individual. The physiological parameter can include at least one of oxygen saturation or SpO$_2$, pulse rate, pleth variability index (PVI), perfusion index (PI), total hemoglobin or SpHb, methemoglobin or SpMet, carboxyhemoglobin or SpCO, conductance, blood glucose concentration or level, insulin concentration or level, glucagon concentration or level. The disease event can correspond to at least one of a heart palpitation or a detected cognitive impairment. The disease event can correspond to the measurement of the physiological parameter failing to satisfy a threshold. The disease event can correspond to changes in the measurements of the physiological parameter. A conductance measure can serve as a measure of sweat, which is another physiological change that occurs during prodromal hypoglycemia. In this way a conductance measurement can act as an additional adjunctive feature to improve the triggering.

The disease management system of any of the preceding paragraphs may also include any combination of the following features described in this paragraph, among others described herein. The one or more processors can be configured to determine confirm that the disease management system is coupled to the individual prior to causing administration of the medication to the individual. The disease management system can include a sensor configured to measure conductance. To determine confirm that the disease management system is coupled to the individual can be based at least on part on the measurement of the conductance. The one or more processors can be configured to cause an alarm indicating to replace adhesive of the disease management system based at least in part on a determination that a conductance measurement does not satisfy a conductance threshold. The disease management system can further include a medication administration device configured to administer the medication with or without interaction from a user.

The present disclosure also provides a method of managing one or more disease events. A disease management system can attach to an individual. The method can include determining a pose of an individual based at least in part on pose information received from a pose sensor attached to an individual, determining a measurement of a physiological parameter based at least in part on physiological data received from a physiological sensor attached to the individual, identifying a disease event based at least in part on the measurement of the physiological parameter, based at least in part on said identifying the disease event and a determination that the pose of the individual corresponds to a first pose, causing an instruction to change poses and based at least in part on said identifying the disease event and a determination that the pose of the individual does not correspond to the first pose, administering a medication to the individual via an administration device, wherein the administration of the medication to the individual causes a change in the physiological parameter.

The method of the preceding paragraph may also include any combination of the following features described in this paragraph, among others described herein. The physiological data can include blood glucose measurement data. The measurement can include a blood glucose measurement. The method can further include performing a calibration procedure to calibrate the pose of the individual relative to a group of known poses. The medication can include rises glucagon. The disease event can correspond to Hypoglycemia. The method can include determining a measurement of conductance, and determining that the disease management system is coupled to the individual based at least on part on the measurement of the conductance. The method of can include determining a measurement of conductance; determining that the disease management system is not coupled to the individual based at least on part on the measurement of the conductance; and determining not to administer the medication to the individual based on said determining that the disease management system is not coupled to the individual.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

DETAILED DESCRIPTION

Figure 1:
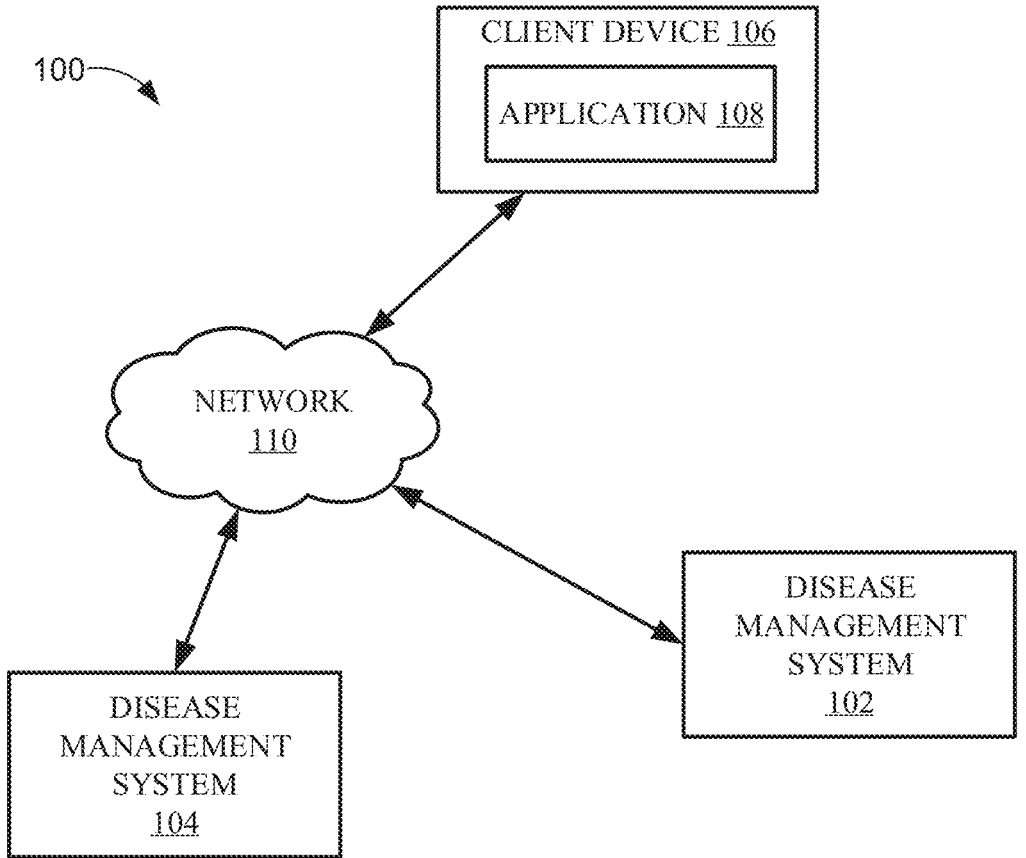
FIG. 1 illustrates an example of a disease management environment.

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

Systems and methods described herein may be applicable to diabetic disease management or another individual condition that may be treated with an implant or other minimally or non-invasive device configured to monitor a patient state and deliver medication on an ongoing or temporary basis. While reference may be made to a specific disease, such as diabetes, systems and methods described herein may be applicable to other diseases and conditions. For example, systems and methods described herein may be applicable to Hypoglycemia, a condition in which an individual's blood sugar level is low, or Hyperglycemia, a condition in which an individual's blood sugar level is high.

While in some examples, systems and methods described herein may reference monitoring or sensing of a specific parameter or blood analyte, such as glucose, other physiological conditions, physiological states, physiological parameters, physiological markers, blood analytes, the like or a combination thereof may be monitored or determined in addition or in the alternative to glucose. Similarly, while in some examples, reference may be made to a specific type of sensor, such as a glucose sensor, other analyte or other sensors may additionally or alternatively be used. For example, a glucose sensor may be configured to additionally measure other analytes. Additionally or alternatively, while reference may be made to specific types of invasive or non-invasive sensors, such as an invasive glucose sensor, any type of invasive or non-invasive sensor may be used, such as a non-invasive analyte sensor.

Additionally or alternatively, while in some examples, systems and methods described herein may reference specific medication, such as insulin or glucagon, to be delivered to the individual, other medications, fluids, or treatments may be administered in addition or in the alternative to medications such as insulin or glucagon. Similarly, while in some examples, reference may be made a specific type of pump or other component associated with a medication or fluid, such as an insulin pump or glucagon pump, the components described herein may be used with any fluid or medication and may include any device or apparatus configured to administer the medication.

Additionally, while reference may be made to the use of a certain number or type of device, any combination and number of devices may be used, such as one, two, three, four or more redundant or different devices. In some examples, a single device may be used to manage aspects of an individual's health, such as a combined medication pump and analyte sensor. In some examples, redundant devices may be used to manage aspects of an individual's health, such as two combined medication pump and analyte sensor devices. In some examples, different devices may be used and in communication to manage different aspects of an individual's health or different aspects of disease management, such as a separate medication pump and analyte sensor. In some cases, administration can include medication injected intramuscularly, subcutaneously, or intravenously or received orally, rectally, or via intranasal spray.

Hypoglycemia refers to a low blood sugar (glucose) level and is a common complication of diabetes. The glucose level that defines hypoglycemia is variable; however, hypoglycemia is defined by the American Diabetes Association as a blood sugar level that is below 3.0 mmol/L (54 mg/dL). In general, symptoms of hypoglycemia do not usually manifest until levels have reached a low of between 2.8 to 3.0 mmol/L (50 to 54 mg/dL). Symptoms can include, but are not limited to, confusion, unconsciousness, tremors, sweating, palpitations, anxiety, depression, tearfulness and feeling of dread, restlessness, dilated pupils, a sensation of pins and needles or tingling, or other symptoms that generally require assistance from another person to treat. If left untreated, severe hypoglycemia can cause seizures, loss of consciousness, and in some cases, it can be fatal (for example, brain death, cardiac arrhythmias, etc.).

It has been discovered that insulin-dependent diabetics average two episodes of symptomatic hypoglycemia per week. Furthermore, research suggests that there may be hundreds of thousands of severe hypoglycemic events and tens of thousands hypoglycemic related deaths annually in the US. As many as 1 in 20 individuals with Type 1 diabetes will die from a hypoglycemic event. Furthermore, data suggests that approximately one-third of older adults with diabetes whom have experienced severe hypoglycemia died within three years of the incident. This evidence suggests that an episode of hypoglycemia may have long-lasting consequences. Accordingly, severe hypoglycemia is an under-recognized risk factor for death in those with diabetes, and the ongoing adoption of insulin regimens will likely continue to increase the number of hypoglycemic events observed annually.

Furthermore, some people may suffer from hypoglycemia unawareness: a complication of diabetes in which the person is unaware of the drop in blood sugar because it fails to trigger the secretion of epinephrine which generates the characteristic symptoms of hypoglycemia that serve to warn the individual of the dropping blood glucose. Hypoglycemia unawareness can result in prolonged exposure to hypoglycemia, which can result in severe side effects including, but not limited to, seizure, loss of consciousness, or brain damage. The development of hypoglycemia unawareness increases the difficulty in managing blood glucose, since the affected individual may not be aware of symptoms until it is too late to treat (for example, because the individual is unconscious) without assistance from another party. About one in five people with Type 1 diabetes and one in ten with insulin-treated Type 2 diabetes report experiencing hypoglycemia unawareness.

Several factors may increase the risk of hypoglycemia unawareness. For example, a drop in blood glucose levels while sleeping can increase the risk of hypoglycemia unawareness. Many people develop nocturnal hypoglycemia while they are asleep and are not awake to perceive the symptoms or treat episode. If this happens frequently, it can affect the individual's ability to detect hypoglycemia warning symptoms while awake. As another example, exercise may increase the risk of hypoglycemia unawareness. The likelihood of hypoglycemia is increased both during and after exercise, when the body's tissues are more sensitive to insulin. This effect can be delayed and occur up to 15 or more hours later, especially if the amount of exercise was unusually strenuous. As another example, having diabetes for a long time may increase the risk of hypoglycemia unawareness. One study found that nearly 50% of people who had used insulin for over twenty years had developed impaired hypoglycemia awareness, while only 20% of those who were on insulin for fewer than ten years experienced this problem. People who have had diabetes for longer are more likely to have been exposed to multiple episodes of hypoglycemia, which has been shown to contribute to hypoglycemia unawareness. As another example, cognitive awareness may increase the risk of hypoglycemia unawareness. As people age, they start to experience cognitive symptoms such as slowed thinking, confusion, and difficulty speaking at the same time as typical hypoglycemia symptoms like shakiness, hunger, or sweating. The cognitive symptoms can therefore interfere with recognition of hypoglycemia. At younger ages, people typically recognize hypoglycemia more frequently because they experience "autonomic" symptoms before "cognitive" symptoms. There is no exact age when this effect begins to take place, as the process of aging varies so widely. However, some studies have shown that hypoglycemia unawareness occurs more frequently in people above the age of 60. As another example, consuming alcohol may increase the risk of hypoglycemia unawareness. Consuming alcohol can, at least in the short term, lower an individual's ability to recognize typical symptoms and impair the liver's ability to release glucose when your blood sugar is too low. These effects typically last as long as it takes your body to process the alcohol.

In contrast to insulin which is a hormone that removes glucose from the blood, glucagon is a hormone that encourages release of glucose into the blood. Glucagon can be used as a tool to help during hypoglycemic events; however, glucagon injections are seldom used due at least in part to its side effects (for example, nausea, vomiting) and/or the typical requirement that a second party aid with the injection.

A glucagon injection generally includes a solution to be mixed in a several step process. The process can vary across embodiments but generally includes a second party (for example, friend, family member, or emergency responder) performing a series of tasks such as removing the syringe and glucagon vial from the case, removing the cap from the needle, removing the cap from the vial, injecting liquid contained in the syringe into the glucagon vial wherein the liquid and freeze-dried glucagon are mixed within the vial, drawing the solution into syringe, and injecting the solution into the individual's leg or abdomen. A liquid glucagon formulation also exists, but the process generally remains reliant on secondary operators.

In situations in which the individual is unconscious due to hypoglycemia, it can be important that the response (for example, the administration of glucagon) be immediate and effective. However, the difficulties inherent in the glucagon kit and process for administering the glucagon make such a response difficult for untrained friends and family. In general, the greater number of steps required to administer the glucagon, the greater opportunity for error and failure. Accordingly, there is need for alternative approaches for glucagon or other medication delivery beyond emergency kits such as those described above. This need is emphasized by a simulation study of injectable glucagon where 50% of caregivers and 80% of acquaintances failed to inject any glucagon and three participants delivered insulin instead of glucagon.

Disclosed is a disease management system configured to reliably, safely, and automatically administer medication to an individual experiencing a disease event, such as hypoglycemia, hyperglycemia, or certain severities of hypoglycemia or hyperglycemia. In this way, the disclosed disease management system can reduce an individual's risk of prolonged exposure to hypoglycemia/hyperglycemia, risk of death, risk of other complications, etc. In some cases, the disclosed disease management system eliminates or reduces a need for second party administration. In some cases, the disclosed disease management system reduces the mental burden of administering the medication, for example by reducing the number of steps to be performed by the individual or a second party. In some cases, as a safety measure, the disclosed disease management system can prevent medication administration while the individual in in certain poses (for example, on his back) and/or can instruct the individual to change poses to receive the medication. In some cases, the disclosed disease management system can include a "bypass" injection features, allowing the individual to initiate an administration. In some cases, the disclosed disease management system is a wearable, implantable, or minimally or non-invasive device.

A disease management system may not be ready to inject a medication due to, for example, warmup periods, stabilization periods, or end of life periods. Disclosed is a disease management system configured to allow a user-initiated injection to allow an individual to cause an injection of medication, for example if the individual knows they are in an emergency situation.

The present disclosure also describes an integrated system that can incorporate a dosage system and physiological measurement sensor into one unit. Various components of the integrated system are described in detail herein, such as various medication pumps and applicators that may be used to apply the unit to an individual.

Environment Overview

FIG. 1 illustrates an example of a disease management environment 100 that includes a disease management system 104, a disease management system 102, a client device 106, and a network 110. To simplify discussion and not to limit the present disclosure, FIG. 1 illustrates only one disease management system 102, disease management system 104, and client device 106, though multiple may be used. Furthermore, it will be understood that the environment 100 can include fewer, different, or additional devices or systems, as desired.

Any of the foregoing components or systems of the environment 100 may communicate, such as via the network 110. Although only one network 110 is illustrated, multiple distinct and/or distributed networks 110 may exist. The network 110 can include any type of communication network. For example, the network 110 can include one or more of a wide area network (WAN), a local area network (LAN), a cellular network (for example, LTE, HSPA, 3G, and other cellular technologies), an ad hoc network, a satellite network, a wired network, a wireless network, Bluetooth, and so forth. In some embodiments, the network 110 can include the Internet. In some cases, two or more of the components or systems of the environment 100 may be connected via a wired connection. In some cases, any one or any combination of the components or systems of the environment 100 may include an Ethernet adapter, cable modem, Wi-Fi adapter, cellular transceiver, baseband processor, Bluetooth or Bluetooth Low Energy (BLE) transceiver, or the like, or a combination thereof.

Any of the foregoing components or systems of the environment 100, such as any one or any combination of the disease management system 104, the disease management system 102, or the client device 106 may be implemented using individual computing devices, processors, distributed processing systems, servers, isolated execution environments (for example, virtual machines, containers, etc.), shared computing resources, or so on. Furthermore, any of the components or systems of the environment 100 may be combined and/or may include software, firmware, hardware, or any combination(s) of software, firmware, or hardware suitable for the purposes described. In some cases, a component or system of the environment 100 can be configured to communicate through another component or system of the environment 100. For example, in some cases, the client device 106 and the disease management system 104 can be configured to communicate through the disease management system 102.

The client device 106 may facilitate monitoring and/or management of one or more blood analytes, such a blood glucose. For example, as described herein, the client device 106 may provide an interface through which a user can interact with, control, or manage one or more of the disease management system 104 or the disease management system 102.

In some cases, the client device 106 device may implement an application 108. For instance, the client device 102 may represent any computing device capable of interacting with or running the application 108. The application 108 may facilitate monitoring and/or management of one or more blood analytes, such a blood glucose. The application 108 may include a web browser, a mobile application or "app," a background process that performs various operations with or without direct interaction from a user, or a "plug-in" or "extension" to another application, such as a web browser plug-in or extension. Although FIG. 1 illustrates the application 108 as being implemented on the client device 102, it will be understood that any of the components or systems of the environment 100 may host, execute, or interact with the application 108.

Examples of client devices 106 may include, without limitation, smart phones, tablet computers, handheld computers, wearable devices, laptop computers, desktop computers, servers, portable media players, gaming devices, and so forth. Furthermore, in some cases, the client device 106 may be integrated with one or more of the disease management system 104 or the disease management system 102.

The disease management system 102 can be used for continuous and/or spot check monitoring of one or more physiological parameters. Generally speaking, there can be at least two ways to obtain physiological parameter measurements. These include continuous monitoring and spot check measuring. A third approach is a hybrid of these two where an individual is monitored continuously for a short period of time to obtain a snapshot of physiological information. Continuous monitoring can involve taking measurements of an individual continuously or at least approximately continuously over an extended period of time. Spot check measurements, on the other hand, are typically performed as a single measurement at one point in time, instead of several measurements over a period of time as in continuous monitoring. A spot check measurement may be performed by placing a sensor on an individual, manually observing some characteristic of the individual, receiving a sample from an individual (for example, accepting and analyzing a test sample, such as via a test strip reader), etc. Like continuous measurements, spot check measurements (sometimes referred to herein simply as "spot checks") may be performed in a hospital or in any other setting, such as at an individual's home.

In some cases, the disease management system 102 may include a sensor that is attachable to an individual and configured to invasively or noninvasively obtain physiological signals. For example, the physiological signals may be obtained from any of a number of sensors including, but not limited to, optical sensors, piezoelectric sensors, electrical sensors, biomechanical sensors, or combinations of the same. For instance, optical sensors may provide parameters such as oxygen saturation or $SpO_2$, pulse rate, pleth variability index (PVI), perfusion index (PI), total hemoglobin or SpHb, methemoglobin or SpMet, carboxyhemoglobin or SpCO, blood glucose concentration or level, insulin concentration or level, glucagon concentration or level, among others. A piezoelectric sensor may be used to calculate parameters such as respiratory rate and pulse rate. Electrical sensors can be used to calculate parameters such as respiratory rate, heart rate, and other ECG-related parameters obtained from the electrocardiogram. Biomechanical sensors, such as bioimpedance sensors, can be also used to capture parameters like respiratory rate. In some cases, the sensor includes a pose sensor, as described herein.

In some cases, the disease management system 102 may be configured to obtain a specimen sample (for example, blood, urine, or other bodily fluid) from a user and can determine one or more physiological parameter measurements based at least in part on the specimen sample. The disease management system 102 can obtain the sample in a variety of ways. For example, the disease management system 102 may include a reception region in which the disease management system 102 can receive a sample via a test strip, swap, container, droplet, etc.

The one or more physiological parameters monitored or determined by the disease management system 102 can vary across embodiments. For example, the one or more physiological parameters can include, but are not limited to, blood glucose concentration or level, insulin concentration or level, glucagon concentration or level, oxygen saturation or $SpO_2$, pulse rate, pleth variability index (PVI), perfusion index (PI), total hemoglobin or SpHb, methemoglobin or SpMet, carboxyhemoglobin or SpCO, respiratory rate, heart rate, among others. The physiological parameter can include temperature of an individual.

Consider a scenario in which the disease management system 102 is configured to obtain measurements associated with blood glucose. In some such cases, the disease management system 102 may include a blood glucose monitor (for example, continuous glucose monitor (or CGM)), a test strip reader, a test strip, a lancet, or a display to display results, etc. For instance, the disease management system 102 can include a blood glucose monitor or sensor similar to that described in U.S. Pat. Pub Nos. 2012/0226117, entitled "Handheld Processing Device Including Medical Applications for Minimally and Noninvasive glucose Measurements," filed Nov. 20, 2011, published Sep. 6, 2012, or 2012/0296178, entitled "Personal Health Device," filed May 16, 2012, published Nov. 22, 2012, each of which is hereby incorporated in its entirety by reference herein.

The disease management system 104 can be used to facilitate administration of a medication to an individual, such as hormones (for example, glucagon, insulin, etc.) or other substances. In some cases, the disease management system 104 may be configured to provide an alert to the individual or a caregiver as to when to perform an administration (for example, intravenously, intramuscularly, subcutaneously in a kit that contains a vial and a syringe). In some cases, the disease management system 104 may be configured to perform the administration. For example, the disease management system 104 may be configured to couple to an individual and perform administrations with or without intervention from a user. In some cases, the disease management system 104 can be implemented as a wearable device that a user can wear directly on their body. As another example, the disease management system 104 can be implemented as an implantable device. In some cases, the disease management system 104, or the combination of the disease management system 104 and the disease management system 102, can provide a closed loop medication administration system, which can allow individuals impacted by particular ailments (for example, diabetes) to go about daily life without having to worry about their insulin or glucose levels, which can vastly improve a diabetic's quality of life.

In some cases, the particular medication (for example, glucagon, insulin, etc.) and/or amount administered is based at least in part on the one or more physiological parameter measurements obtained by the disease management system 102. For example, in some cases, the disease management system 104 can administer medications to the individual in order to regulate or affect the one or more physiological parameters measured by the disease management system 102. Consider a scenario in which the disease management system 102 is monitoring blood glucose. In some such cases, the disease management system 104 may facilitate the administration of insulin or glucagon to the individual based on the levels of blood glucose in the individual. For instance, based at least in part on a determination that a user's blood glucose level does not satisfy a blood glucose threshold (for example, indicating that blood sugar levels are too low), the disease management system 104 can cause or cause or perform administration (for example, of glucagon) or end an administration (for example, of insulin). As another example, based at least in part on a determination that a user's blood glucose level satisfies a second blood glucose threshold (for example, indicating that blood sugar levels are too high), the disease management system 104 can cause or perform administration (for example, of insulin) or end an administration (for example, of glucagon).

The disease management system 104 may be utilized as an emergency or backup administration system. For example, the disease management system 104 may trigger an administration during a life threatening situation, such as when a user's blood sugar levels are too high or too low. Furthermore, in some cases, the disease management system 104 may cause an audible, visual, or other indication to alert the user that a life threatening situation is occurring, to alert the user that administration is or will be occurring, to provide instructions to the user.

In some cases, the disease management system 104 is configured to administer medication. In some cases, the disease management system 104 can deliver the medication within a threshold period of time. In some cases, the disease management system 104 can eliminate or reduce the need for second party assistance. In some cases, the disease management system 104 requires little or no interaction from a user in order to administer the medication to the individual. In some cases, the disease management system 104 is easy to apply and remove. In some cases, the disease management system 104 is configured to stay on the body. In some cases, the disease management system 104 is small in size so as the minimize body real estate requirements. In some cases, the disease management system 104 is discreet. In some cases, the disease management system 104 has remote administration capability, for example, via the client device 106. In some cases, the disease management system 104 has longer device wear times. In some cases, the disease management system 104 is water resistant or water proof. In some cases, the disease management system 104 is not greatly affected by altitude, humidity, or temperature.

Figure 2:
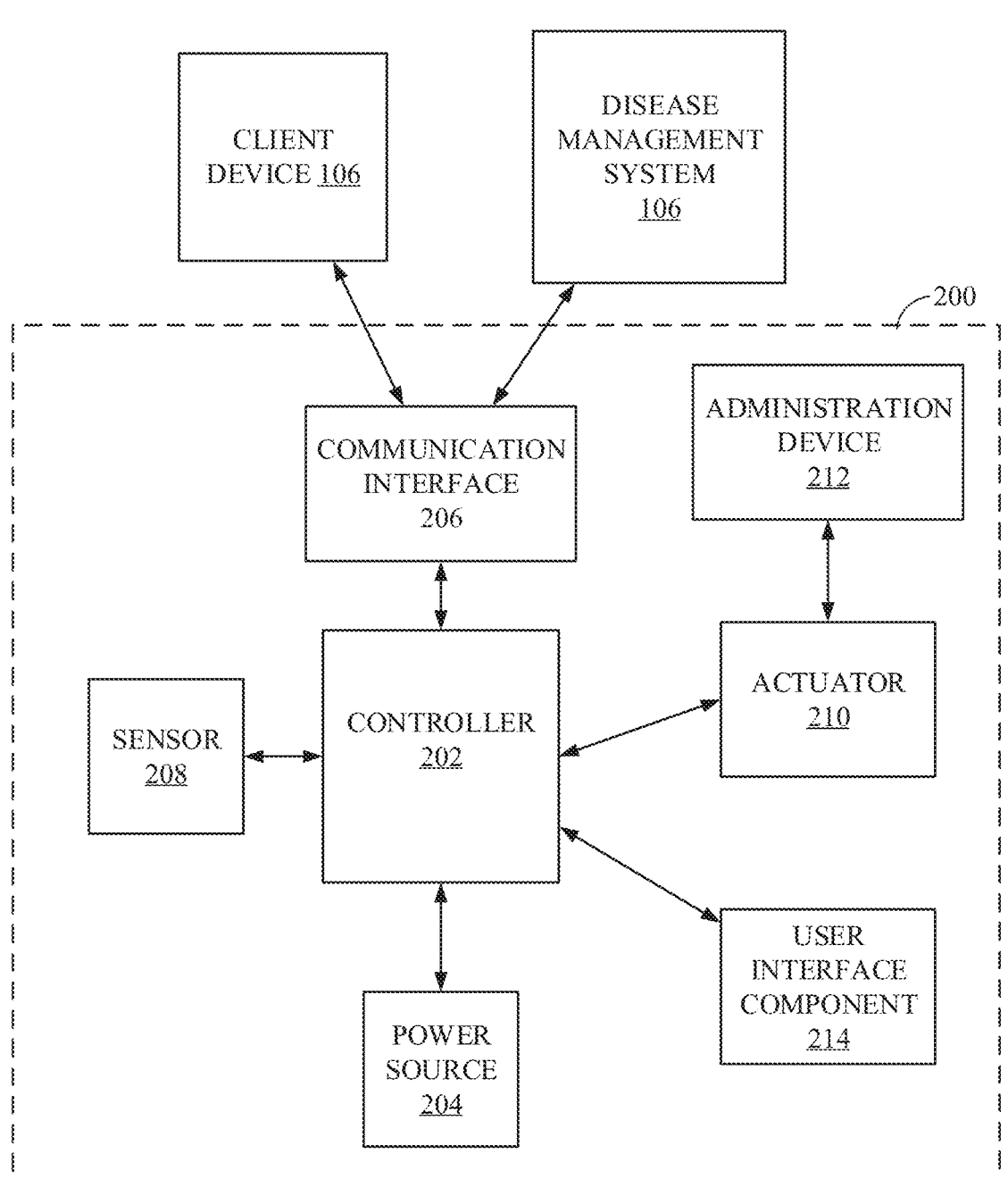
FIG. 2 illustrates a block diagram of an example disease management system.
Figure 3A:
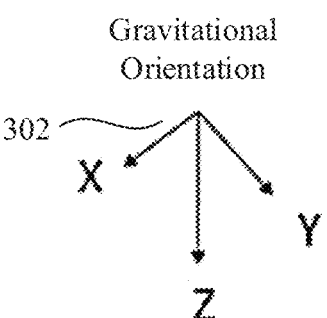
FIGS. 3A-3E illustrate example poses of an individual and an example pose sensor attached to the individual at the various poses.
Figure 3A:
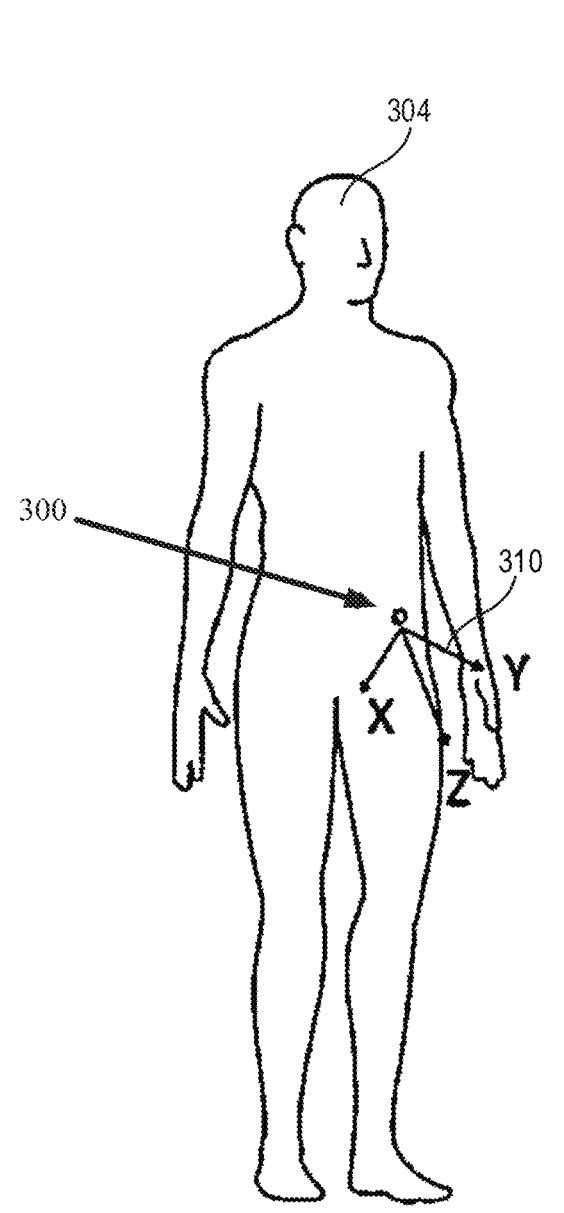
Figure 3B:
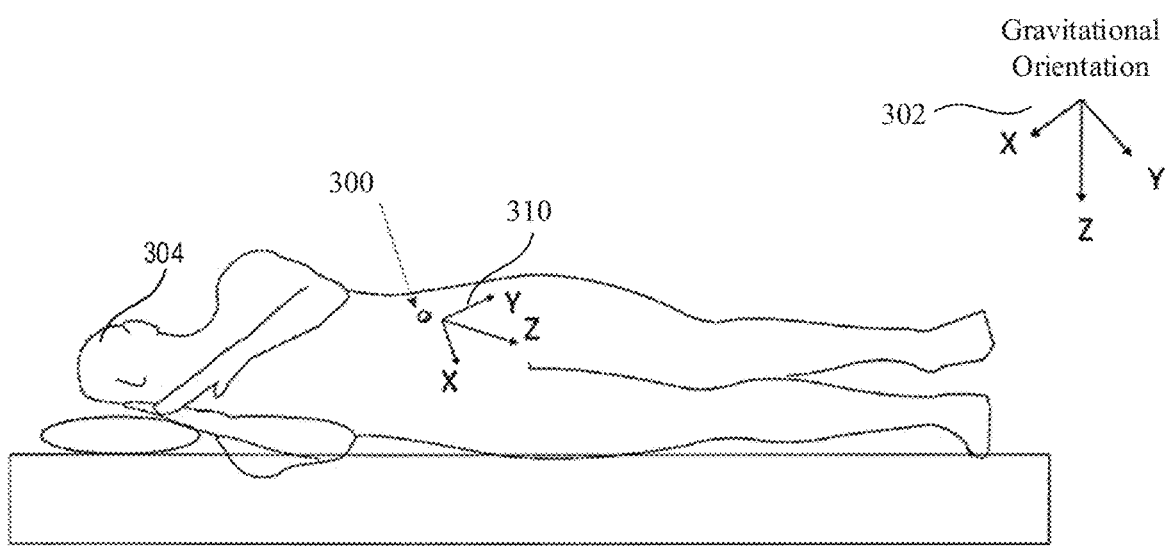
Figure 3C:
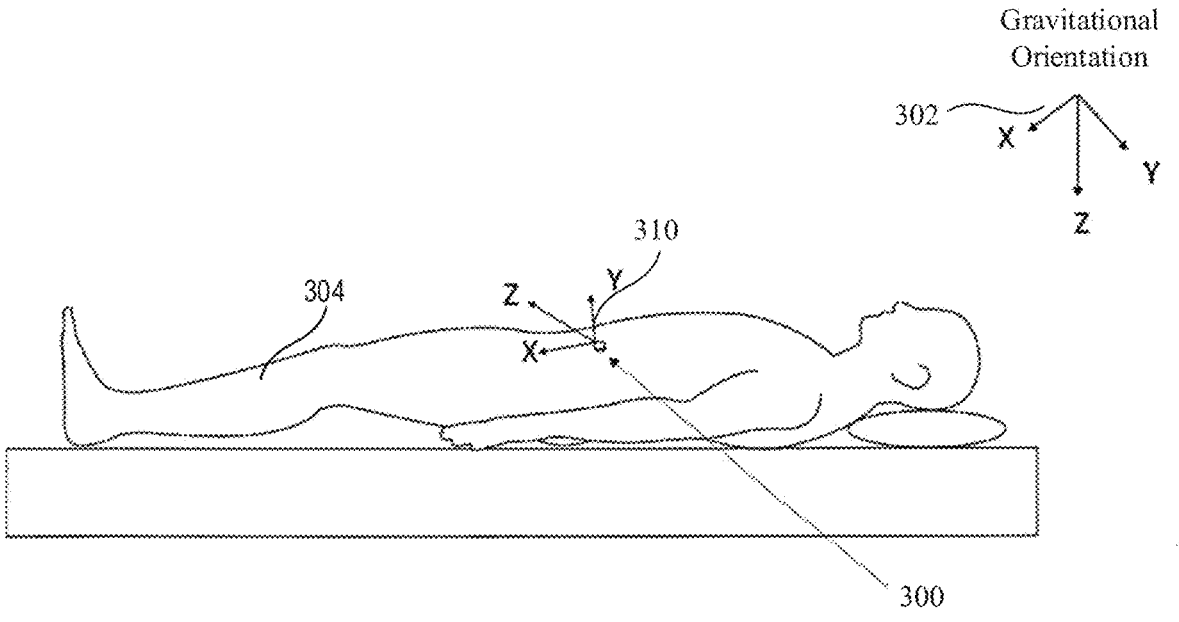
Figure 3D:
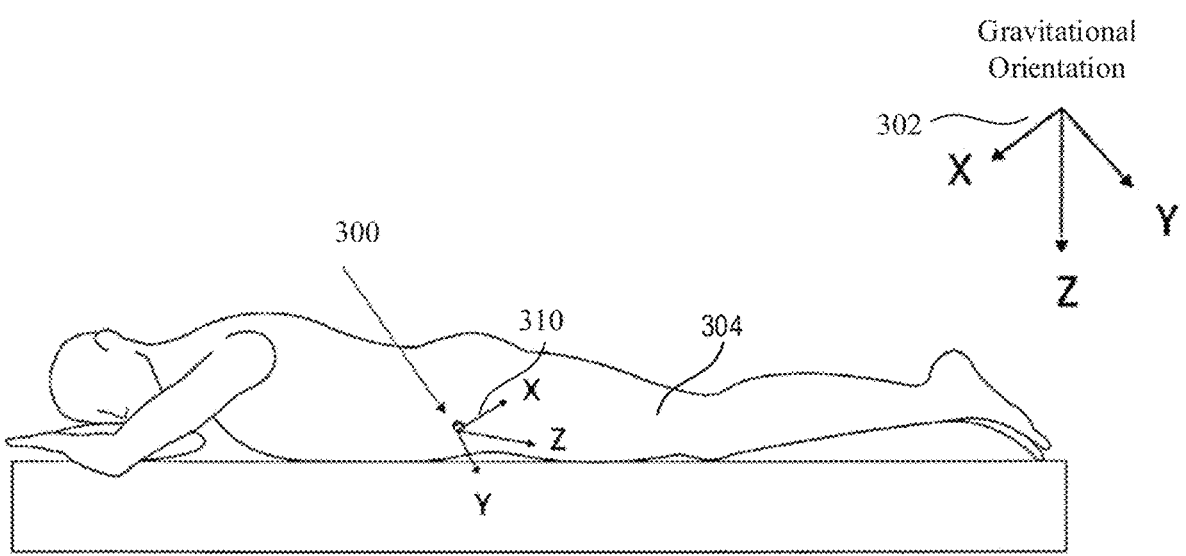
Figure 3E:
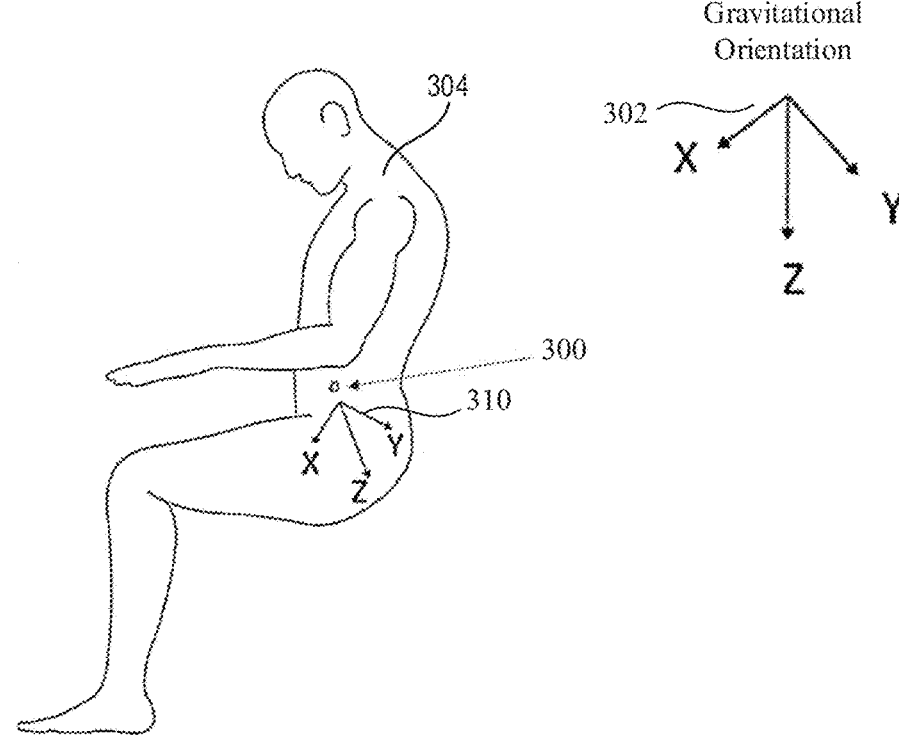

FIG. 2 illustrates a block diagram of an example disease management system 200, which may be an embodiment of the disease management system 104 of FIG. 1. As shown, the disease management system 200 can include a controller 202, a power source 204, a communication interface 206, a sensor 208, an actuator 210, an administration device 212, or a user interface component 214. However, it will be understood that the disease management system 200 can include fewer, different, or additional devices or systems, as desired.

Although the disease management system 200 is shown as separate from the disease management system 102 and client device 106, in some cases, the disease management system 200 can include or be integrated with the disease management system 102 or client device 106.

The power source 204 can provide power to the disease management system 200. For example, the power can include a power supply (for example, one or more batteries, a wall outlet connector, etc.) and electronics to drive the controller 202, communication interface 206 (for example, transceiver), sensor 208, actuator 210, administration device 212, or user interface component 214.

The communication interface 206 can facilitate wired or wireless communication with one or more other systems or devices, such as the disease management system 102, the client device 106, the application 108, the network 110, etc. For example, the communication interface 206 can include a transceiver that includes an antenna. The communication interface 206 can be configured for any of a variety of applications, such as satellite technology (e.g. GPS), Bluetooth, BLE, Wi-Fi, near-field communication (NFC), mobile networks (e.g. 3G and 4G), or any combination thereof.

In some cases, the disease management system 200 can be configured to provide an alter based on the identification of a disease events. The alert can include an audible, visual, vibrotactile or other indication. For example, in some cases, the alert may include turning on the GPS, activating location services, enabling a 3G/4G/5G system, or the like in response to an identification of a disease event. This alert would enable localization of the person in emergency.

The sensor 208 can include a pose sensor configured to obtain pose data usable to determine a pose of an individual. The term "pose" is a broad term encompassing its plain and ordinary meaning and may refer to, without limitation, position and/or orientation or any other appropriate location information. The pose sensor can include, but is not limited to, any one or any combination of an accelerometer, gyroscopes, orientation sensor, gravity sensor, GPS or other location-related device, etc. The sensor 208 can include a physiological sensor, as described herein. For example, the disease management system 200 can receive physiological data and determine measurements of one or more physiological parameters, similar to the disease management system 200, as described herein. The sensor information may be processed and communicated to the controller 202. Similarly, the controller 202 may receive physiological data, such as from the disease management system 102.

The combination of the actuator 210 and the administration device 212 can deliver medication. For example, in some cases, the medication can include glucagon, a hormone that raises blood glucose levels. Although implementations can vary across embodiments, in some cases, the actuator 210 can be part of a medication pump that can administer medication to an individual with or without input from the individual.

The user interface component 214 can include one or more buttons, switches, speakers, microphones, displays, or any combination thereof. For example, the user interface component 214 can include a speaker for alarms, such as voice directed alarms. As another example, the user interface component 214 can include a screen for a visual display or one or more status light indicators. In some cases, the user interface component 214 can be part of the client device 106.

The controller 202 can process data, such as sensor data from the sensor 208, or data received from the disease management system 102 or the client device 106. In some cases, controller 202 is capable of executing an application or providing a graphical user interface, which may be interacted with by a user to adjust settings, administer glucose, pair with other devices, calibrate, or the like.

Continuous glucose monitors (CGMs) measure the body's blood glucose (blood sugar) levels in real-time by sensing the glucose present in tissue fluid. CGMs are often configured to trigger an alarm when the blood sugar is too low (Hypoglycemia) or too high (Hyperglycemia). CGMs are often configured to trigger an alarm when the patient's blood sugar is too low or too high. These alarms have proven valuable in efforts to reduce the likelihood of conditions such as diabetic comas or the "dead-in-bed" syndrome. However, some manufacturers require alarms that cannot be silenced. Furthermore, many manufacturers require sensitive alarm settings, which tend to produce numerous false-alarms. The false-alarm, coupled with the inability to silence the alarms, can cause sleep disruption or insomnia.

Traditionally, the CGM alarm settings can be associated with a "time to react." The time to react can be related to an expected needed to perform a sequence of events (for example, wake up, take a validation measurement while possibly impaired, administer a lifesaving emergency glucagon syringe) before losing consciousness, which occurs around 20 mg/dL. Table 1 illustrates various blood sugar thresholds (in mg/dL) and the expected amount of time (in min) to react at those thresholds. As shown, when assuming a maximum possible physiologic rate of change of glucose of −3 mg/dL, an individual with a blood sugar of 70 mg/dL has approximately 16 minutes to mitigate her condition before she becomes unconscious. Further, an individual with a blood sugar of 60, 50, and 40 mg/dL has approximately 13, 10, and 7 minutes, respectively, to mitigate her condition before she becomes unconscious. The traditional minimum non-silenceable alarm is set to 50 mg/dL.

TABLE 1

Blood sugar levels and expected time to react before unconsciousness.

| Threshold [mg/dL] | Time to react [min] |
| --- | --- |
| 70 | 16 |
| 60 | 13 |
| 50 | 10 |
| 40 | 7 |

Disclosed herein is a disease management system that can address at least the aforementioned or other concerns. For example, the disease management system can allow the minimum non-silenceable alarm to be lowered, thereby reducing the number of false alarms and reducing the instances of sleep disruption or insomnia. In addition or alternatively, the disease management system can address safety concerns of administering glucagon. For example, by monitoring an orientation of the individual, the disease management system can prevent administration of glucagon to an individual while the individual is lying on his back, thereby reducing the risk of choking given that glucagon administration tends to cause vomiting.

Continued false alarms are expected to continue to make persons with diabetes lifestyle difficult. This is due to the expectation that today's CGMs will not produce accuracy beyond 8% MARD (due to lag-time issues) and that control algorithms will take on more function for the user autonomously. Some manufacturers require alarms that cannot be silenced and produce general insomnia as a result. One way of addressing this issue is by mitigating the issue of hypoglycemia. Alarms are set very high because a subject can only manage their state if they are conscious. If a device were to have a failsafe measure to manage the hypoglycemic state, one could argue the limit could be brought lower and remove a significant number of false alarms.

Regarding the conventional sensitive alarm settings, the disease management system provides a device to manage the hypoglycemic state, which can allow the minimum non-silenceable alarm to be lowered. For example, in the event of a life-threatening situation relating to blood sugar, the disclosed disease management system can automatically administer glucagon to the individual. Table 2 illustrates various blood sugar thresholds (in mg/dL) and the expected amount of time (in min) to react at those thresholds. As shown, the threshold when using the disclosed disease management system can be safely lowered to 40 mg/dL, thereby significantly reduce false-alarms.

TABLE 2

Blood sugar levels and expected time to react before unconsciousness.

| Threshold without emergency glucose [mg/dL] | Time to react [min] | Threshold with emergency glucagon [mg/dL] |
| --- | --- | --- |
| 70 | 16 | 50 |
| 60 | 13 | 45 |
| 50 | 10 | 40 |
| 40 | 7 | 30 |

The administration of certain medications (for example, glucagon) can often induce vomiting. For example, some studies suggest that glucagon induces vomiting 36% 18% of the time. Accordingly, prior to administering the medication to an individual, it can be prudent to ensure that the individual is not in a pose (for example, lying on his back) that might lend to choking, should vomiting ensue.

To address these or other concerns, disclosed herein is a disease management system configured to determine a pose of an individual. Based on the pose, the disease management system can determine whether to administer the medication. In some cases, if the disease management system determines that the pose corresponds to any of a groups of poses that might lend to choking, the disease management system can refrain from administering the medication for a period of time and/or activate an alarm or instruction to attempt to cause the individual to change her pose or move to a particular pose so that the medication can be more safely administered. In this way, the disease management system reduces the likelihood that an individual will choke, should the medication cause the individual to vomit.

FIGS. 3A-3E illustrate example poses of an individual 304 and an example pose sensor 300 worn by, implanted in, or otherwise attached to the individual 304 at the various poses. In particular, FIGS. 3A-3E illustrate the following poses: standing, lying on side, lying on back, lying on stomach, and sitting up, respectively.

Furthermore, FIGS. 3A-3E illustrate relative orientation axes 310 of the pose sensor 104 at the various poses and also illustrates gravitational orientation axes 302. In these examples, the orientation and/or position of the individual is at least temporarily fixed relative to the relative orientation axes 310 of the disease management system 104. Due to this fixed relationship, the relative orientation axes 310 change as the pose of the individual changes. Accordingly, in some cases, the pose of the individual 304 can be quantified or determined based on the relative orientation axes 310. For example, a particular relative orientation axes 310 (+/− an offset) can be associated with a particular pose or set of poses. In this way, the disease management system can determine a pose of the individual based on the relative orientation axes 310. In some cases, the disease management system can determine a pose of the individual the using the relative coordinate system features in a multivariate distribution confidence, learned neural network, or other classification system.

As described herein, in some cases, a lying on back pose may be identified as an unsafe pose for administering medication, while any of a standing pose, lying on side pose, lying on stomach pose, sitting up pose may be identified as a safe pose for administering medication. In some such cases, based on a determination that the pose of the user is lying on back pose, the disease management system can determine to at least temporarily refrain from administering medication. As a corollary, based on a determination that the pose of the user is not a lying on back pose, the disease management system can determine administer the medication.

In some cases, a disease management system can calibrate the individual frame of reference from the relative frame of reference to detect the individual body position. For example, the pose of the disease management system on the user's body can be quantified. In some cases, the pose of a user during sleep could be quantified relative to the pose of the device on the user's body during sleep as described in the four states—side, back, stomach, and out of scope.

In some cases, to correlate the readings of the pose sensor 300 with various stored relationships between poses and the relative orientation axes 310, the disease management system can be configured to calibrated the pose sensor 300 according to a calibration policy. The calibration policy may indicate to calibrate the pose sensor 300 at predetermined intervals of time (such as every X number of seconds, or every X minute(s)), or in response to a particular event (such as the attachment of the disease management system to the individual 304, turning on the power of the disease management system, user input, etc.).

Figure 4:
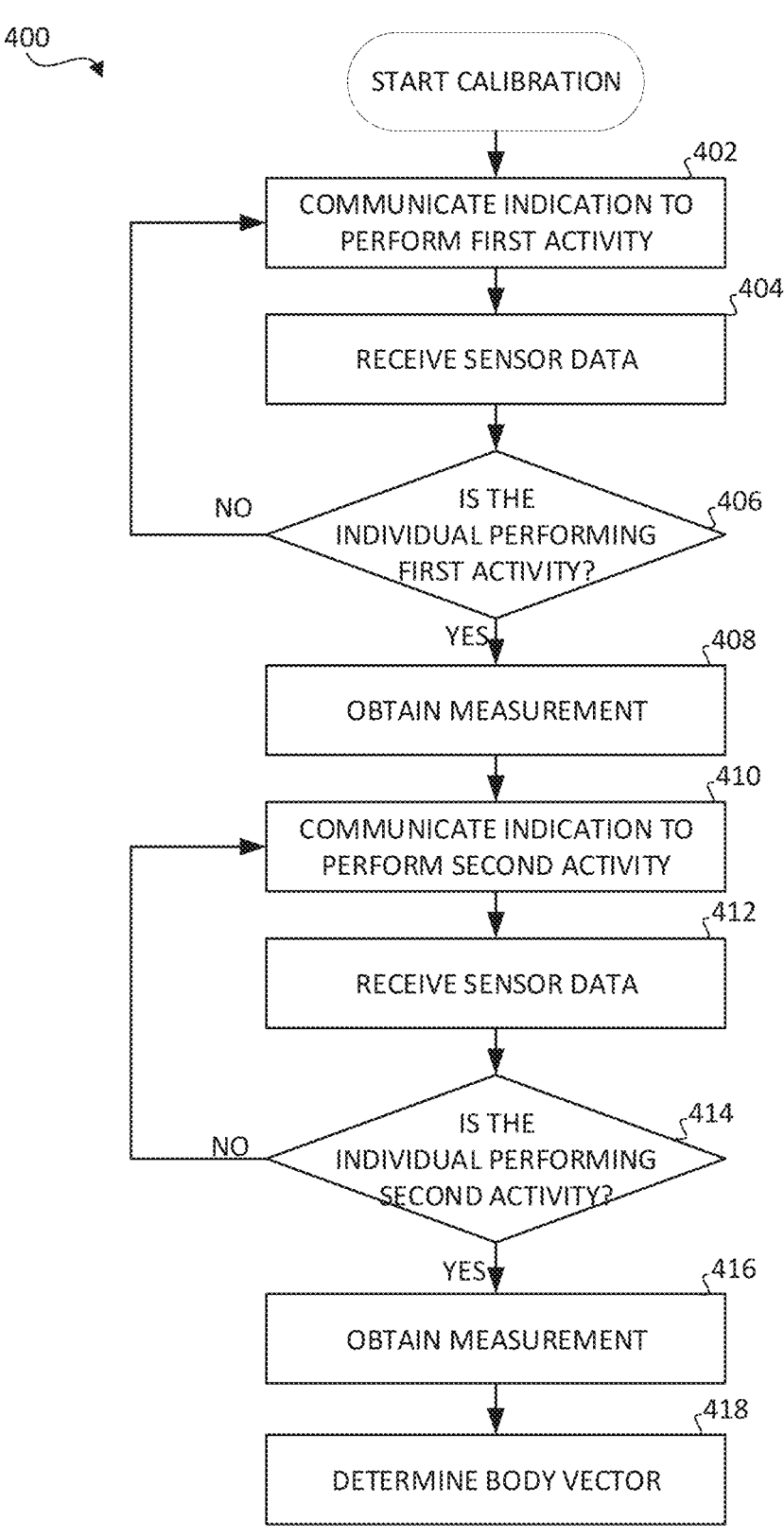
FIG. 4 illustrates a flow diagram for an example calibration to determine a pose of a user.

FIG. 4 illustrates a flow diagram for an example calibration to determine a pose of a user. The elements outlined for process 400 can be implemented by a processing device, such as the controller 202 of the disease management system 200. For ease of reference, the process 400 has been logically associated to the disease management system 200.

At block 402, the disease management system 200 communicates a first instruction indicating for an individual to perform a first activity. The first activity can vary across embodiments. For example, the first activity can correspond to any of various poses or movements including, but not limited to, standing, sitting upright, lying on back, lying on side, lying on stomach, walking, running, crouching, pulling knees to chest, etc. For purposes of this example, the first activity is standing. In general, a standing position includes standing still, in an upright or vertical position, with the head centered over the shoulders, with the chin up, with the feet slightly less than shoulder width apart, and with the back and legs substantially straight. However, a standing position can vary based on the individual.

The first instruction can be audible, visual, vibratory, etc. For example, in some cases, the disease management system 200 can cause a display or other visual indicator to indicate that the individual should perform the first activity. In some cases, the disease management system 200 cause a display to display words, such as "stand up," or a visual representation of an individual standing. In some cases, the disease management system 200 can cause a visual indicator to light up or otherwise indicate that the calibration is starting. It will be understood that a visual indication to stand up can occur in various ways and these illustrative examples should not be construed as limiting.

In some cases, the first instruction can include a verbal command. For example, the disease management system 200 can cause a speaker to instruct the individual to perform the first activity. In some cases, the speaker can be configured to play a particular sound to indicate that the user should perform the first activity. In some cases, the speaker can be configured to play an audible messages, such as "stand up." It will be understood that a verbal or other indication to stand up can occur in various ways and these illustrative examples should not be construed as limiting.

In some cases, the disease management system 200 may not communicate a first instruction indicating for the individual to perform the first activity. For instance, in some cases, the individual can perform the first activity without receiving an instruction and the calibration procedure may initiate in response to the individual performing the first activity.

At block 404, the disease management system 200 obtains a set of pose data from the pose sensor 300. As described herein, the pose sensor 300 can include, but is not limited to, one or more accelerometers, gyroscopes, orientation sensors, gravity sensors, GPS units, or a combination thereof.

At block 406, the disease management system 200 determines whether the individual is performing the first activity based at least in part on the set of pose data. In some cases, the disease management system 200 can determine that the individual is performing the first activity based on a general determination of whether the pose data is changing over time. In some cases, the disease management system 200 can determine whether the individual is moving based on a gravity vector of the sensor data. For example, if the norm of the gravity vector is less than gravity ($\|\vec{a}\| < g$), then the disease management system 200 can determine that the individual is not moving.

If the pose data is changing over time, then the disease management system 200 can determine that the individual is moving and therefore is not performing an action which requires the individual to be still (for example, standing). As a corollary, if the pose data is not changing over time, then the disease management system 200 can determine that the individual is not moving and therefore is not performing an action which requires the individual to be moving (for example, walking, running).

Consider an example in which the first activity is standing. In some such cases, based on a determination that the pose data (for example, accelerometer data) is changing over time, the disease management system 200 can determine that the individual is moving and is therefore likely not standing. Accordingly, the disease management system 200 can transition back to block 402 to communicate the instruction to stand.

In contrast, based on a determination that the pose data (for example, accelerometer data) is not changing over time, the disease management system 200 may determine that the individual is not moving and is therefore likely performing the first activity (for example, standing). Based on a determination that the individual is likely performing the first activity, the disease management system 200 can transition to block 408 to communicate the instruction to stand.

At block 408, the disease management system 200 stores the pose data as a measurement for the first activity. In some cases, the pose data includes a gravity vector ($\vec{a}$).

At block 410, similar to block 402, the disease management system 200 communicates a second instruction indicating for the individual to perform a second activity. The second activity can be different from the first activity and can correspond to any of various poses or movements including, but not limited to, standing, sitting upright, lying on back, lying on side, lying on stomach, walking, running, crouching, pulling knees to chest, etc. For purposes of this example, the first activity is walking in a straight line. Similar to the first instruction described herein, the second instruction can include any of audible, visual, tactile, or other indications.

At block 412, similar to block 404, the disease management system 200 obtains a set of pose data from the pose sensor 300.

At block 414, the disease management system 200 determines whether the individual is performing the second activity based at least in part on the set of pose data. If the disease management system 200 determines that the individual is not performing the second activity, the disease management system 200 can transition back to block 410. If the disease management system 200 determines that the individual is performing the second activity, the disease management system 200 can transition to block 416.

Consider a scenario in which the second activity is walking. In some cases, the disease management system 200 can determine that the individual is walking based on the pose data. For example, if the norm of d less gravity is in the range of the acceleration expected of walking ($w_{min}<\|$ $\vec{a}\|-g<w_{max}$), then the disease management system 200 can determine that the individual is walking.

In some such cases, the disease management system 200 can determine that the individual is not walking based on a determination that the individual is not walking, or is performing some activity that does not correspond to walking. For instance, based on a determination that the individual is spinning or standing still, the disease management system 200 can determine that the individual is not walking. The disease management system 200 can determine whether the individual is spinning based on accelerometer data and gyroscope data. If the gyroscope norm is some rotational threshold above a noise floor ($\|\vec{gyro}\|<rot_{thresh}$), then the disease management system 200 can determine that the individual is not spinning.

At block 416, the disease management system 200 stores the pose data as a measurement for the second activity. In some cases, the pose data includes a second vector measurement ($\vec{b}$).

At block 418, the disease management system 200 determines the individual's body vector ($\hat{b}$) based on the measurement ($\vec{a}$) for the first activity and the measurement ($\vec{b}$) for the second activity. For example, the process can use the following relationships to determine the body vector ($\hat{b}$):

$$\vec{v} = \vec{a} \times \vec{b} \qquad \text{(Equation 1)}$$

$$\vec{c} = \vec{a} \cdot \vec{b} \qquad \text{(Equation 2)}$$

-continued $$S = \begin{bmatrix} 0 & -v_3 & v_2 \\ v_3 & 0 & -v_1 \\ -v_2 & v_1 & 0 \end{bmatrix} \qquad \text{(Equation 3)}$$

$$R = I + S + S^2 * \frac{1-c}{\|\vec{v}\|^2} \qquad \text{(Equation 4)}$$

$$\hat{b} = R * \vec{a} \qquad \text{(Equation 5)}$$

where $\vec{a}$ is the standing measurement, $\vec{b}$ is the walking measurement, $\hat{b}$ is the body vector, S is the skew matrix. In some cases, as part of verification of standing still, the norm of the vector $\vec{a}$ should be less than gravity, such that $\|\vec{a}\|<g$, where g is gravity. Additionally, in some cases, the norm of the vector d less g should be in the range of acceleration expected of walking such that $w_{min}<\|\vec{a}\|<w_{max}$ Similarly, in some cases, the gyroscope norm should be some rotational threshold just above the noise floor such that $\|$ $\vec{gyro}\|<rot_{thresh}$.

Fewer, more, or different blocks can be used as part of the routine 400. In some cases, one or more blocks can be omitted. In some embodiments, the blocks of the routine 400 can be combined with any one or more of any other blocks. In certain examples, the disease management system 200 can identify when a user is walking a straight line. This identification could be completed via an empirical estimation by machine learning. For example, upon repeated identifications the vectors can be averaged or trim median for a better estimate of the user's true body vector.

This calibration the disease management system 200 can be performed over time to ensure that the disease management system 104 has not changed its body location. For example, the disease management system 200 can occur at predetermined intervals of time, such as every X number of seconds, or every X minute(s), etc., or can occur automatically responsive to a particular event, such as when the individual begins wearing the disease management system 104 or after the passage of a predetermined period of time. In addition or alternatively, the calibration can be initiated by the individual, such as via the user interface component 214. In some cases, if the body vector estimate goes out of distribution, the disease management system 104 can request the initiate the disease management system 200 or the disease management system 104 it may automatically perform some or all of the disease management system 200.

Figure 5:
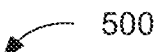
FIG. 5 is a flow diagram illustrative of an example of a routine implemented by a disease management system for identifying a disease event and administering medication to an individual.
Figure 5:
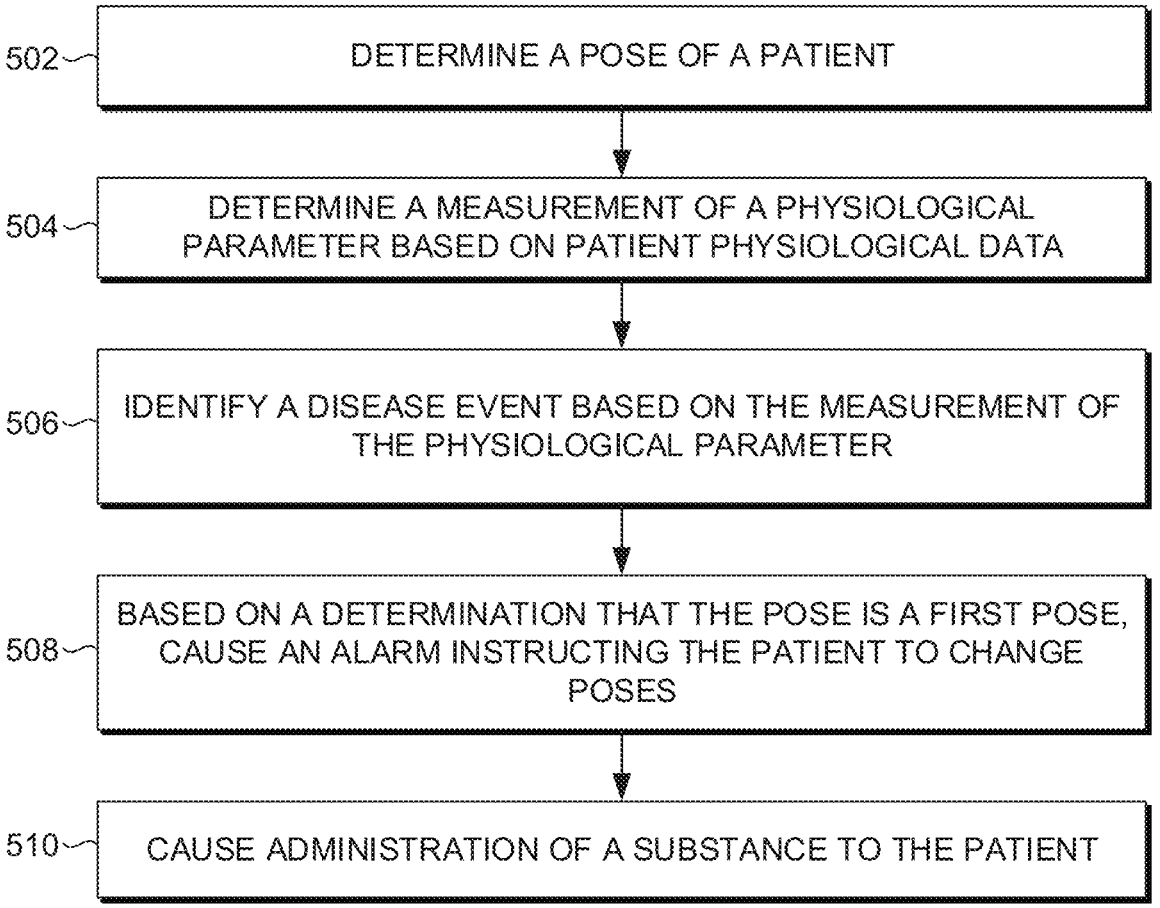

FIG. 5 is a flow diagram illustrative of an example of a routine 500 implemented by a disease management system 200 for identifying a disease event and administering medication to an individual. Although described as being implemented by the disease management system 200, it will be understood that one or more elements outlined for routine 500 can be implemented by one or more computing devices or components that are associated with the disease management environment 100, such as, but not limited to, the disease management system 102, the disease management system 104, the client device 106 and/or the application 108. Thus, the following illustrative embodiment should not be construed as limiting.

At block 502, the disease management system 200 determines a pose of an individual. As described herein, the disease management system 200 system can receive pose data from a pose sensor and can compare the received pose data to stored data. For example, a data store can store information associating pose data with various poses, such a range of pose values that correspond to each pose. In some cases, the disease management system 200 determines the pose to be one of four possible poses: side, back, stomach, and out of scope. However, it will be understood that various other poses are contemplated, such as standing, sitting up, walking, etc.

At block 504, the disease management system 200 determines one or more measurements of one or more physiological parameters based at least in part on physiological data. As described herein, the one or more physiological parameters can include, but are not limited to, blood glucose concentration or level, insulin concentration or level, glucagon concentration or level, oxygen saturation or SpO$_2$, pulse rate, pleth variability index (PVI), perfusion index (PI), total hemoglobin or SpHb, methemoglobin or SpMet, carboxyhemoglobin or SpCO, respiratory rate, heart rate, among others.

At block 506, the disease management system 200 identifies a disease event based on the one or more measurements. The disease event can vary across embodiments. For example, the disease event can correspond to one or more of hypoglycemia, hyperglycemia, a heart palpitation, or cognitive impairment, a level of blood sugar, a change in blood sugar, among others. For example, the disease management system 200 may identifies a disease event based on a determination that blood glucose satisfies or does not satisfy one or more blood glucose thresholds. To identify the disease event, the disease management system 200 can monitor one or a combination or two or more physiological parameters, as described herein.

At block 508, the disease management system 200 determines whether the pose of the individual is an acceptable pose for receiving a medication. As described herein, it can be dangerous to administer some medications to users that are in certain poses (for example, lying on back). Accordingly, the disease management system 200 can determine whether the user is an acceptable pose prior to administering the medication. In some cases, acceptable poses can include any pose other than a lying on back pose. In some cases, acceptable poses can include poses that are unlikely to cause the user to choke, should the medication make the user vomit. For example, acceptable poses can include, but are not limited to, standing, on one's stomach or side, walking, sitting up, or the like.

If the disease management system 200 determines that the pose is not an acceptable pose for receiving a medication, the disease management system 200 can cause the individual to change poses. For example, the disease management system 200 can output an alarm or other indication for the purpose of instructing the user to change her pose or switch her pose to an acceptable pose. In some cases, the disease management system can continue to perform block 508 until the individual is determined to be in an acceptable pose.

At block 510, the disease management system 200 causes administration of the medication to the individual. As described herein, the disease management system 200 can include an administration device, such as a pump, needle, etc.

Fewer, more, or different blocks can be used as part of the routine 500. In some cases, one or more blocks can be omitted. In some embodiments, the blocks of the routine 500 can be combined with any one or more of any other blocks. In certain examples, the disease management system 200 can perform a calibration procedure, such as routine 400, prior to performing routine 500.

Figure 6:
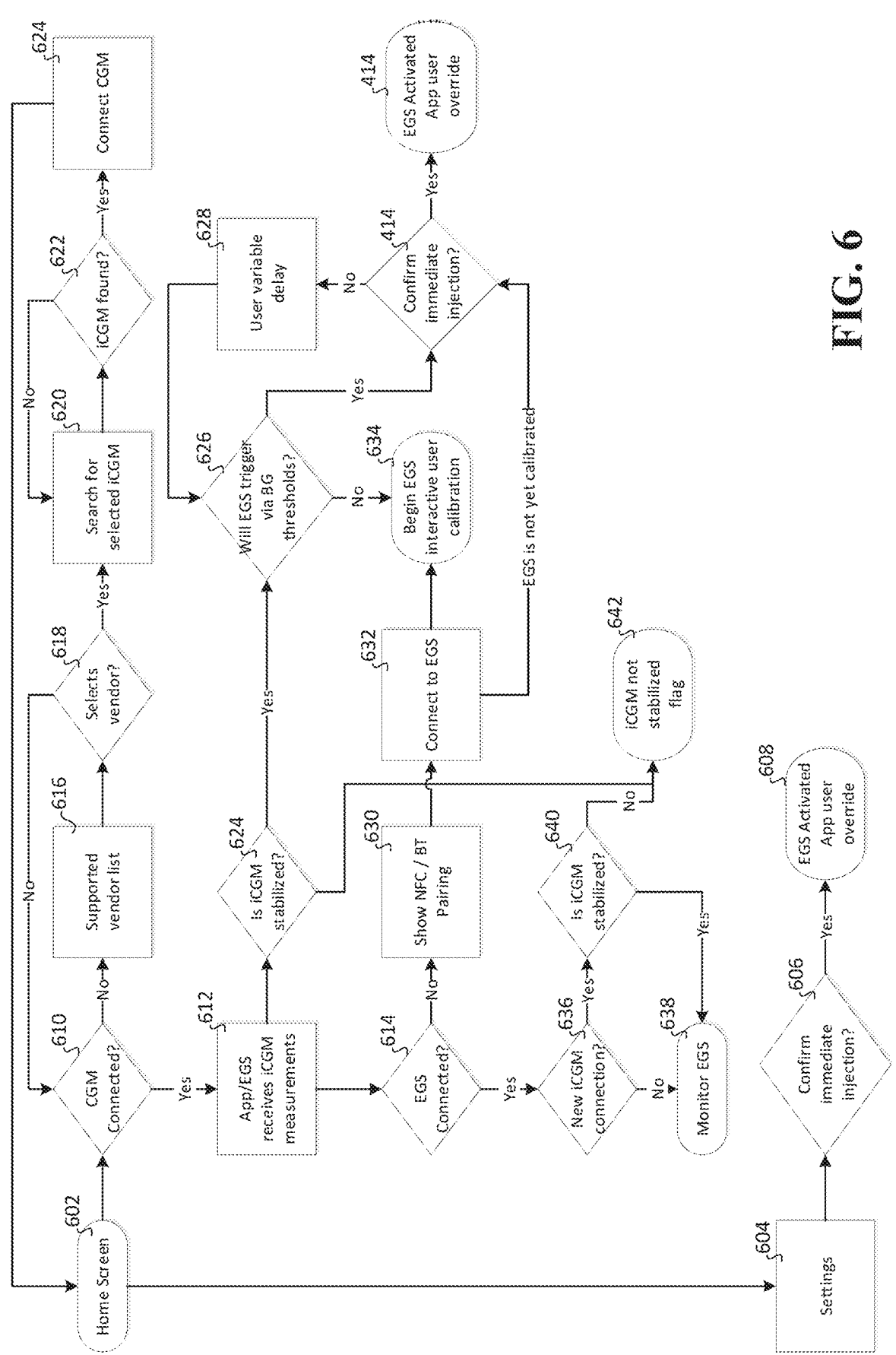
FIG. 6 illustrates a flow diagram associated with an example application for controlling the disease management system, pairing the disease management system with other devices or systems, calibrating the disease management system, etc.

FIG. 6 illustrates a flow diagram associated with an example application for controlling the disease management system 104, pairing the disease management system 104 with other devices or systems, calibrating the disease management system 104, etc. The application can be implemented by a processing device, such as the controller 202 of the disease management system 104, or the client device 106. For example, an application interface can be displayed on a display.

In some cases, it may be desirable to administer medication before the disease management system 104 has been calibrated. For instance, the user's blood sugar may not exceed a threshold blood sugar. In some such cases, the user may be able to administer an immediate injection by activating a user override 606. As illustrated in FIG. 6, starting from the home screen 602, the user can enable a manual injection mode from the settings 604 and confirm the immediate medication injection 606. In some cases, to make injection safe and verified as the user's choice, a fingerprint, passcode, or other security measure may be utilized to ensure this is what the individual really wants.

In some cases, it may be desirable to connect a disease management system 102 to the disease management system 104 after the disease management system 104 has been calibrated. In some such cases, the disease management system 104 may only activate if the disease management system 102 reports it has completed its stabilization period. As illustrated in FIG. 6, at block 610, the application checks to see if a disease management system 102 is connected. If the disease management system 102 is connected, at block 612 the application receives measurement from the disease management system 102. At block 614, the application checks whether a disease management system 104 is connected. If a disease management system 104 is connected, at block 614, the application checks whether the disease management system 102 is a new connection. If the disease management system 102 is a new connection, the application proceeds to block 640, where the application checks if the disease management system 102 is stabilized.

Figure 7:
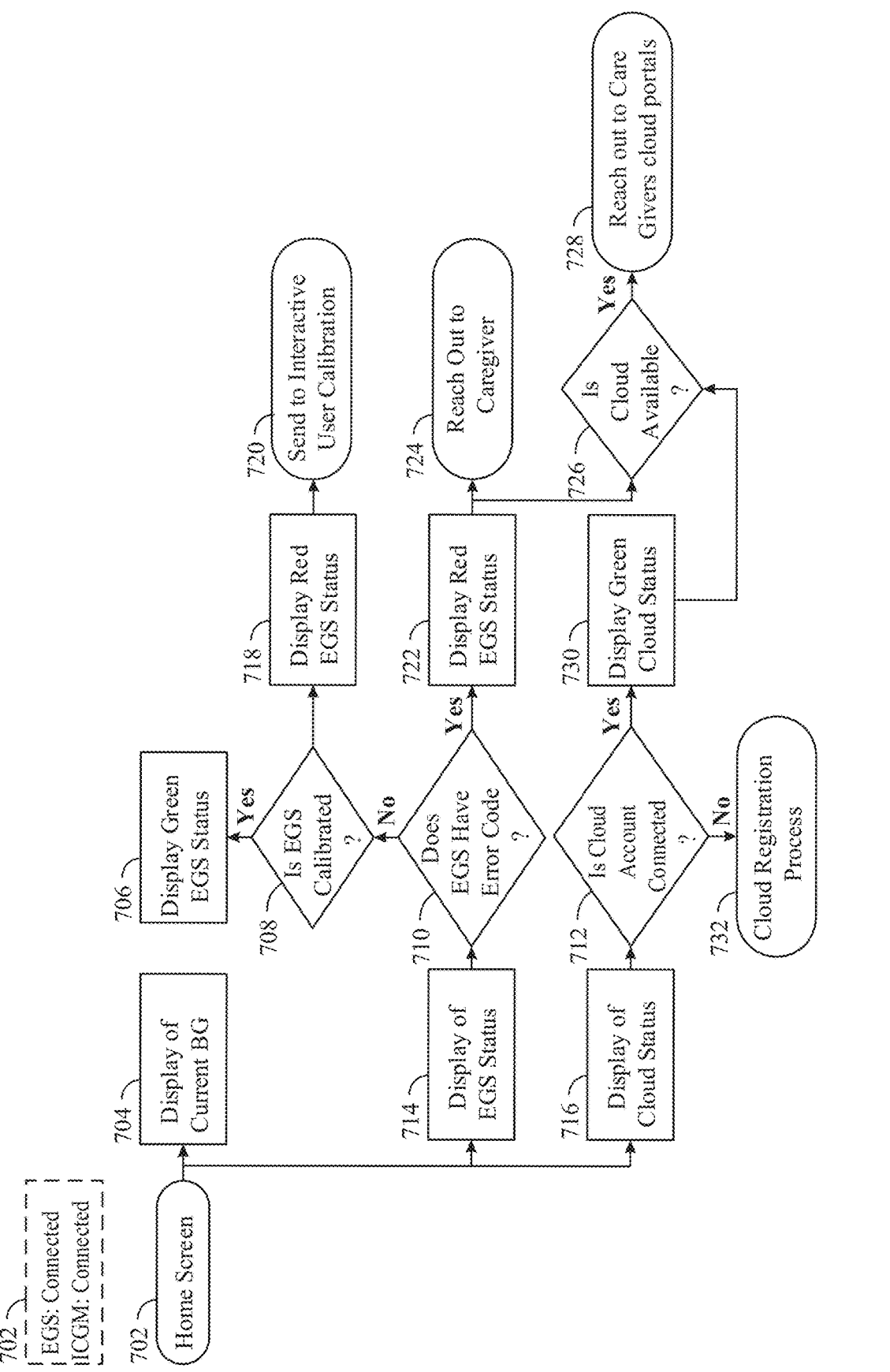
FIG. 7 illustrates a flow diagram for an example monitoring process of an application.

FIG. 7 illustrates a flow diagram for an example monitoring process of an application, such as application 108. As shown by block 702, in this example, the disease management system 104 (sometimes referred to as "EGS") and the disease management system 102 (sometimes referred to as iCGM) are already connected. In this example, the application can include a home screen 702, and the home screen 702 can display various information such as, but not limited to, status of iCGM (or current blood glucose 704), status of EGS 714, and status of Cloud or network connectivity 716. In an emergency state, having these statuses available can aid the user to notify caregivers should hypoglycemia or severe hypoglycemia occur.

With respect to the status of the disease management system, the application can indicate, or be configured to indicate, whether the disease management system has an error code (block 710 or whether the disease management system is calibrated (block 708). For example, application may display various indicators to visually show the status. For instance, a green EGS status (block 706) may indicate that the disease management system does not have an error code and is calibrated. A red EGS status (block 718 or 722) may indicate that the disease management system has an error code or is not calibrated. In some cases, the application may automatically, or allow the user, to repair status issues. For example, if not calibrated, it can be sent to interactive user calibration 720, and if it has an error code, a notification can be send to the caregiver 724.

With respect to the display of cloud status, the application can show if the cloud is connected 712 via a green status indicator 730. If the cloud is not connected, the application can allow a cloud registration process 732.

In some cases, the disease management system 104 is not always awake. For example, the disease management system 104 can wake at predetermined intervals of time, such as every X number of seconds, or every X minute(s), etc., or can wake responsive to a particular event, such as in response to user input, when the individual begins wearing the disease management system 104, or after the passage of a predetermined period of time. In some cases, the disease management system 104 wakes as often as is necessary.

In some cases, at the time of waking the disease management system 104, it can go through a process to ensure delivery of warnings, alerts, or prediction of the system going out of calibration (for example, responsive to the user changing the device orientation on their body).

Figure 8:
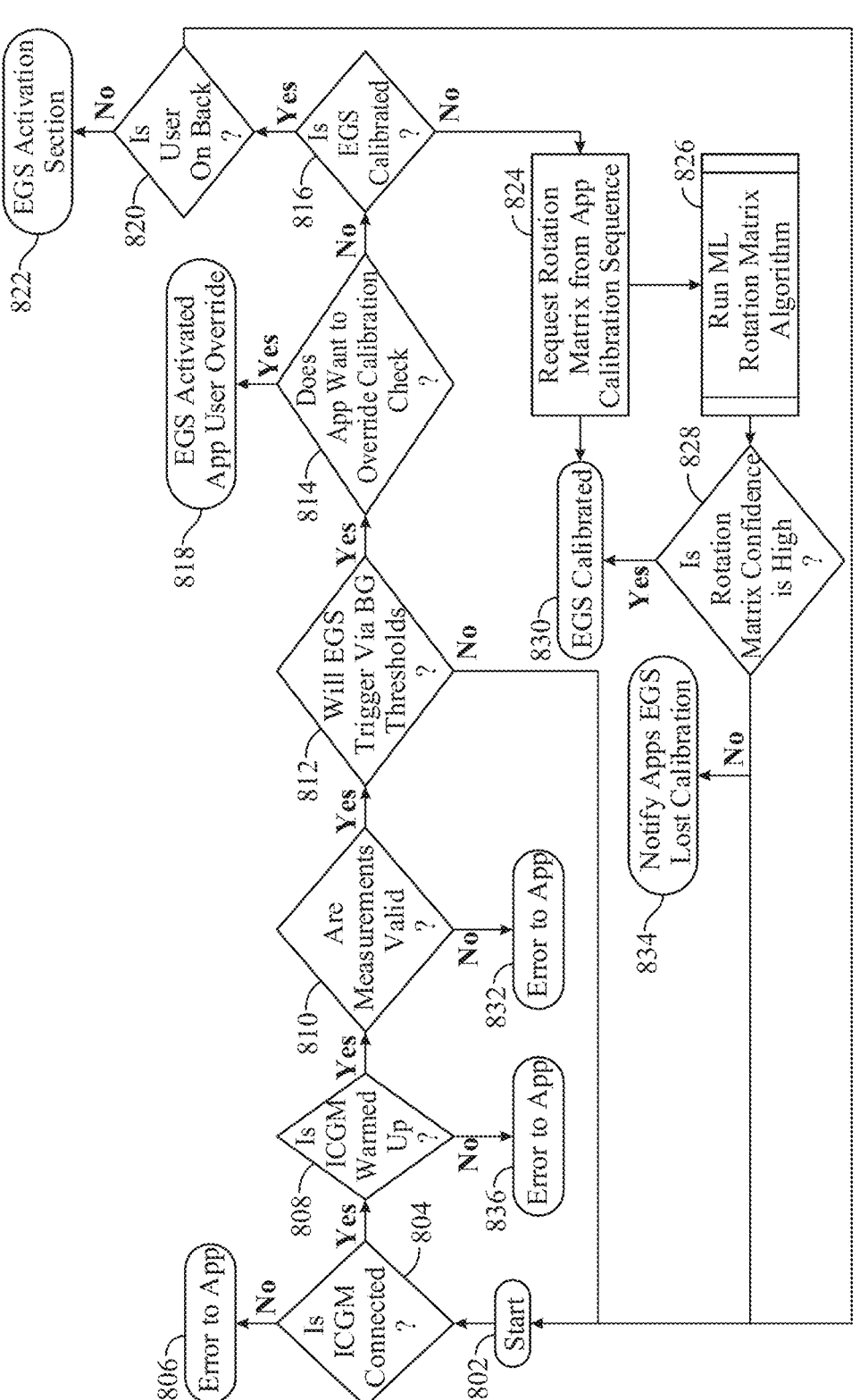
FIG. 8 illustrates an example process performed by the disease management system after waking.

FIG. 8 illustrates an example process or checklist performed by the disease management system 104 after waking. At 804, the disease management system checks to see whether a disease management system 102 is connected. If a glucose system is not connected, it sends an error 806.

At 808, the disease management system 104 checks to see whether the disease management system 102 is warmed up. If not, disease management system 104 sends an error 808.

At 810, the disease management system 104 checks to see whether the measurements from the disease management system 102 are valid. If not, disease management system 104 sends an error 832.

At 812, the disease management system 104 checks to see whether the disease management system 104 will trigger via the blood glucose thresholds. If not, the process returns to start 802. If yes, then the disease management system 104 checks to see whether the application wants to override the calibration check. If yes, the application is overridden 818. If not, the disease management system 104 calibrated 816, for example, using process 500 of FIG. 5.

The administration of medication can occur in any of various ways, such as automated activation, activation before calibration, or manual activation.

Figure 9:
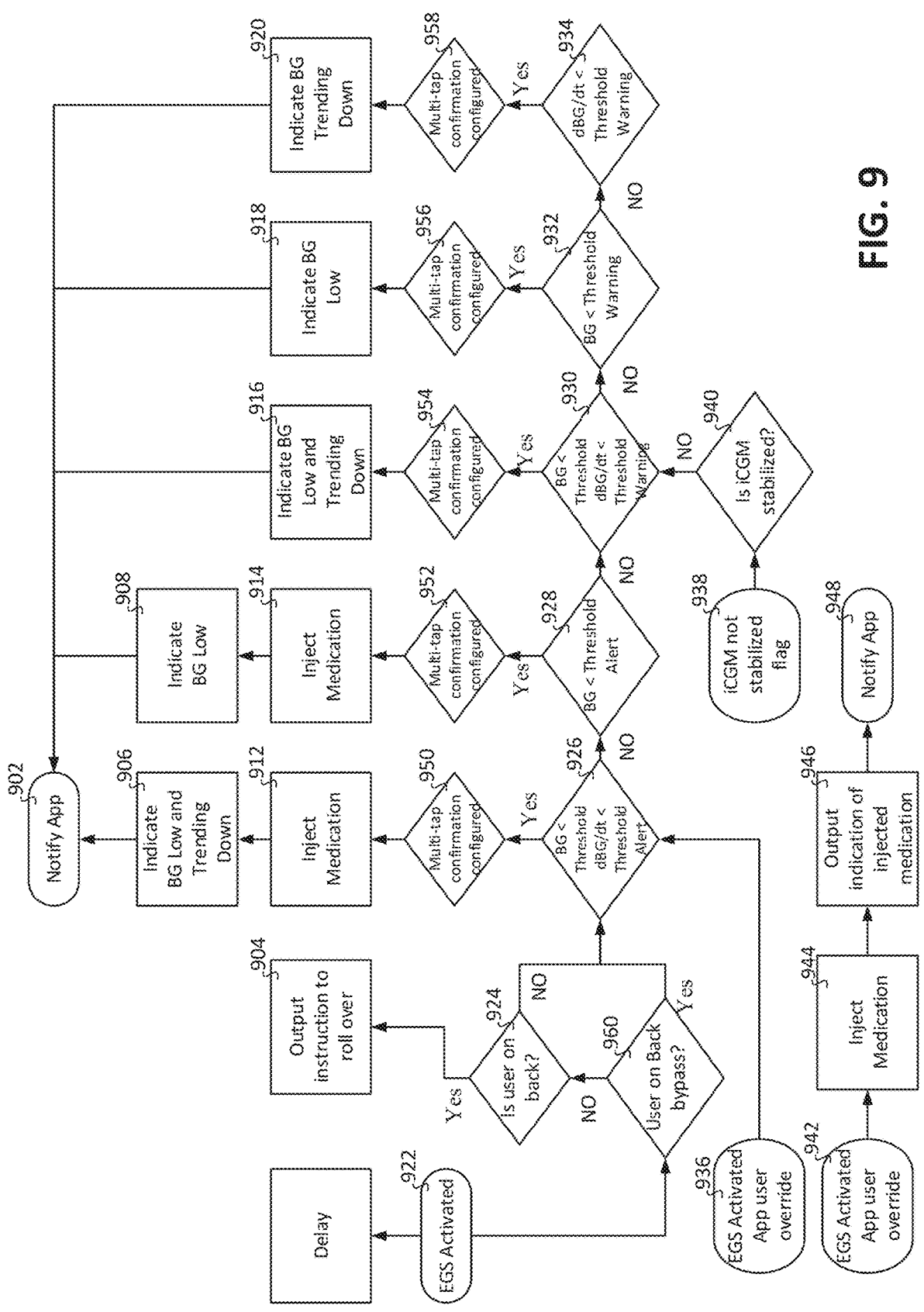
FIG. 9 illustrates a process for administering medication from the disease management system.

FIG. 9 illustrates a process for administering medication from the disease management system 104.

At block 922, the disease management system 104 is activated or turned on. At block 960, the disease management system 104 determines whether the user is attempting to bypass the check that prevents administration is the user is on her back. If the user wishes to implement the bypass, the disease management system 104 proceeds to block 926. If the disease management system 104 does not wish to implement the bypass, the disease management system 104 proceeds to block 924.

At block 924, the disease management system 104 can check if the user is on their back. If so, at block 904, the disease management system 104 can provide an indication (for example, a verbal command) to roll over. For example, in some cases, the disease management system 104 can repeatedly exclaim, "ROLL OVER." It is expected a semiconscious person will respond to such an exclamation so that the medication can more safely be administered. If the user is determined to not be on her back, the disease management system 104 proceeds to block 926.

At block 926, the disease management system 104 determines whether the blood glucose concentration (BG) is less than a blood glucose threshold and/or a threshold rate of change of the blood glucose. If yes, at block 950, the multi-tap confirmation is configured; at block 912, the medication (for example, glucagon) is injected; and at block 906, an indication is output indicating that the blood glucose is low and is trending down. If no, the disease management system 104 proceeds to block 928.

At block 928, the disease management system 104 determines whether the blood glucose concentration (BG) is less than a blood glucose threshold. If yes, at block 952, the multi-tap confirmation is configured; at block 914, the medication (for example, glucagon) is injected; and at block 908, an indication is output indicating that the blood glucose is low. If no, the disease management system 104 proceeds to block 930.

At block 930, the disease management system 104 determines whether the blood glucose concentration (BG) is less than a blood glucose threshold and/or a threshold rate of change of the blood glucose. If yes, at block 954, the multi-tap confirmation is configured; and at block 916, an indication is output indicating that the blood glucose is low and is trending down. If no, the disease management system 104 proceeds to block 932.

At block 932, the disease management system 104 determines whether the blood glucose concentration (BG) is less than a blood glucose threshold. If yes, at block 956, the multi-tap confirmation is configured; and at block 918, an indication is output indicating that the blood glucose is low. If no, the disease management system 104 proceeds to block 934.

At block 934, the disease management system 104 determines whether the rate of change of blood glucose concentration (BG) is less than a blood glucose threshold. If yes, at block 958, the multi-tap confirmation is configured; and at block 920, an indication is output indicating that the blood glucose is trending down.

Triggers can occur via a combination of rate of change and absolute value or just absolute value. Earlier responses can be activated if it is observed the user is trending down. Potentially even earlier responses can occur if a model of the user's glucose-insulin meal model is running in the embedded device.

The system may also support a user's choice (an agreement in terms in and conditions for use) to pre-emptively select how they would like the device to respond in the event of a life critical situation. For example, a user may opt to bypass the "Is User on Back?" of callout 924 if the system deems they are in need of an injection. The user may agree to accept the inherent risk associated with life-saving glucagon administration while on their back. In another situation the user may choose to opt out of injection altogether even if they are on their back and a user forcibly requests the system to inject remotely. In yet another situation the user may configure the system to require a double or triple tap confirmation once the alarm sounds before the system is allowed to administer glucagon.

In some cases, the thresholds used to trigger an alarm can also be modified to further reduce false-positives or false negatives, for example by using adjunctive information to make a more informed decision. Examples of adjunctive information that can be derived from an accelerometer or gyroscope can include the detection of variables such as: seizure related movements, or fall detection. Both of these events can occur during the onset of severe hypoglycemia. Knowledge of these states can be coupled to a simple linear or non-linear adjustment to the glucose offset or rate of change.

Another form of adjunctive information includes any information that can be sent (in addition to CGM values) from a cloud, EHR, or EMR database, or bluetooth connection. Information such as pulse rate could be analyzed to produce a classification of arrhythmia. Arrhythmia is another common form of severe hypoglycemia. The raw waveform, pulse rate, pulse rate variability, or any other non-invasive parameter such as an amount of light absorbed, transmitted through, or reflected at a tissue site, path length (for example, distance that light travels through the material), concentration of an analyte, bioimpedance, tissue dielectric constant, pulse pressure variation (PPV), pleth variability index (PVI®), stroke volume (SV), stroke volume variation (SVV), peripheral capillary oxygen saturation (SpO$_2$), mean arterial pressure (MAP), central venous pressure (CVP), pulse pressure (PP), perfusion index (PI), total hemoglobin (SpHb®), carboxyhemoglobin (SpCO®), methemoglobin (SpMet®), oxygen content (SpOC®), or acoustic respiration rate (RRa®), among other parameters could be pushed to an EGS device to help adjunctively decide to modify how action is taken to administer a live saving dose of medicine. These may also be used to adjunctively modify the EGS threshold for administration.

Sleep can also be used as a feature to adjunctively modify the EGS threshold for administration. The usage of the accelerometer to detect movement and other transceived information (such as pulse rate, PRV, RRa) can be used to assess the depth of sleep. Knowledge of the depth of sleep can then be used to modify the EGS threshold for administration.

Exercise can also be used as a feature to adjunctively modify the EGS threshold for administration. The usage of the accelerometer to detect movement and other transceived information (such as pulse rate, PRV, RRa) can be used to assess the vigor of exercise. Knowledge of the vigor of exercise can then be used to modify the EGS threshold for administration.

Hydration can also be used as a feature to adjunctively modify the EGS threshold for administration. The usage of the accelerometer to detect movement, conductance, absorptive measures, and other transceived information (such as pulse rate, PRV, RRa) can be used to assess the hydration state. Knowledge of the hydration state can then be used to modify the EGS threshold for administration.

Other factors related to the individual records or questionnaires can also be used to adjunctively modify the EGS threshold for administration. These features may include: height, age, sex, weight, ethnicity, time since onset of disease, medications in use, hypoglycemia history, past infusion set issues, scar tissues or lipodystrophy, whether the individual uses inhaled or intramuscular injections, allergies, menstruation, pubescence state, comorbidities, family histories, use of sedatives, sleeping pills or pain medications, hypothyroidism, severe liver disease, malnutrition and malabsorption, insulinomas or group-associated decision making bias.

An EGS system can also be advantageously connected to a lifestyle tracking system such as MyFitnessPal or da vinci to adjunctively modify the EGS threshold for administration. Useful features may include: carbohydrate quantity, food type, macro nutrients micro nutrients, carbohydrate type, glycemic indexes, timing of intake, other ingredients such as caffeine, alcohol, hydration status. Similar information can be obtained from other types of logging apps (or above) such as medication dosing and timing, medications interactions and response history, vitamin intake, activity logging, stress, menstruation, other blood glucose or analyte measurements, sunburn, altitude, frequency of glucose checking, or social circumstance.

The disease management system 104 may be configured to attached to a user. For example, the disease management system 104 can be adhered to a user's skin. In some cases, the disease management system 104 can be configured to attach, un-attached, or re-attached to a user's skin, regardless of skin type and without causing, or causing very little, hard to the skin.

With adhesives, there are at least two variables to consider: the duration on the body and the holding force. In some cases, the disease management system 104 can be attached to a bandage that is replaceable at a high frequency (for example, every day, every few days). For example, the disease management system 104 can include an over-bandage or a replaceable bandage that slides or rotates into place in the bottom of the disease management system 104.

In addition or alternatively, it may be advantageous to reduce the holding force of the adhesive. For example, the integrated holding force over area may be maintained to match the puncture force in an equal and opposite manner. Therefore, one could make a larger bandage with lower holding force that would continue to match the puncture force of the injection needle. The inverse would also be true for a smaller bandage, it would need a higher holding force.

In some cases, it can be important for the disease management system 200 to be adequately adhered to a user's skin. Otherwise, the administration device (for example, a needle) may activate but fail to deliver the correct dosage of medication. For example, the needle may end up in the epidermis or in unpunctured skin above the device, never to be utilized by the individual.

Figure 10:
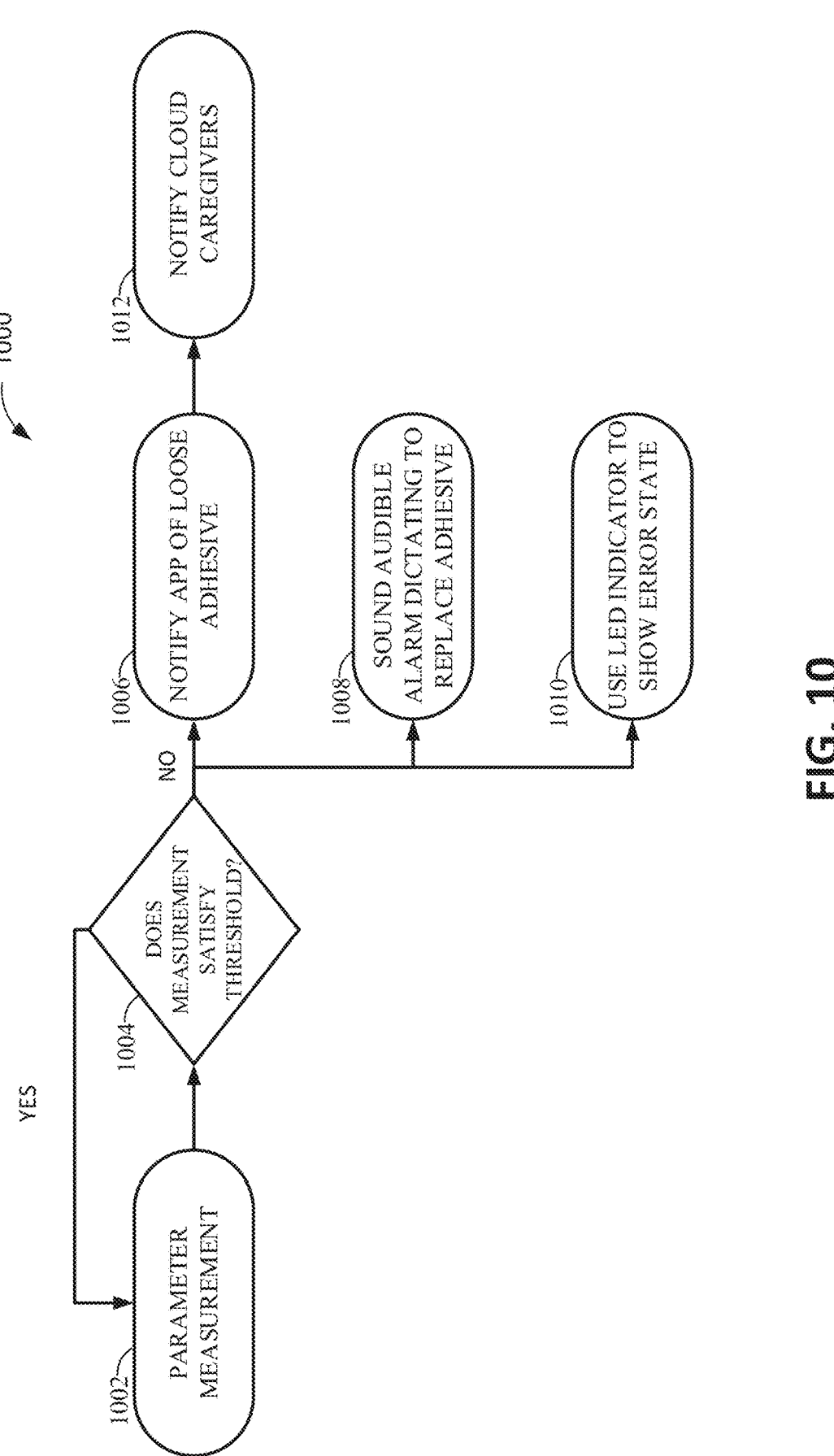
FIG. 10 is a flow diagram illustrative of an example of a routine implemented by a disease management system for identifying whether adhesive has been compromised or come loose from the user's body or around the puncture site.

FIG. 10 is a flow diagram illustrative of an example of a routine 1000 implemented by a disease management system 200 for identifying whether adhesive has been compromised or come loose from the user's body or around the puncture site. Although described as being implemented by the disease management system 200, it will be understood that one or more elements outlined for routine 1000 can be implemented by one or more computing devices or components that are associated with the disease management environment 100, such as, but not limited to, the disease management system 102, the disease management system 104, the client device 106 and/or the application 108. Thus, the following illustrative embodiment should not be construed as limiting.

At block 1002, the disease management system 200 obtains a conductance measurement. For example, the disease management system 200 may include a conductivity sensor configured to measure the ability of a solution to conduct an electrical current. It is the presence of ions in a solution that allow the solution to be conductive: the greater the concentration of ions, the greater the conductivity. In some cases, the disease management system 200 may utilize a conductance measurement across the threshold of the needle puncture zone.

At block 1004, the disease management system 200 determines whether the conductance measurement is in range. The range can vary across embodiments. In some cases, based on a determination that the conductance measurement satisfies a threshold, the disease management system 200 can determine that the conductance measurement is in range and that the adhesive has not been compromised or come loose from the user's body. In some cases, based on a determination that the conductance measurement does not satisfy a threshold (for example, a standard skin conductance range), the disease management system 200 can determine that the conductance measurement is not in range and/or that the adhesive has been compromised or come loose from the user's body.

At blocks 1006, 1008, 1010, 1012, the disease management system 200 outputs an indication that the adhesive has been compromised or come loose from the user's body. For example, at block 1006, the disease management system 200 causes a notification on an app, such as the application 108; at block 1008, the disease management system 200 causes an audible alarm indicating to replace the adhesive; at block 1010, the disease management system 200 causes an LED or other visual indicator to indicate an error state; and at block 1012 the disease management system 200 notifies caregivers via a network. It will be understood that the indication that the adhesive has been compromised or come loose from the user's body can vary across embodiments and that any of blocks 1006, 1008, 1010, or 1012 or other blocks can be utilized to provide the indication.

Terminology

Conditional language used herein, such as, among others, "can," "could," "might," "may," "for example," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

Depending on the implementation, certain acts, events, or functions of any of the processes or algorithms described herein can be performed in a different sequence, can be added, merged, or left out altogether (for example, not all described operations or events are necessary for the practice of the algorithm). Moreover, in certain implementations, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the disclosure herein can be implemented as electronic hardware (for example, ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the disclosure herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. A processor device can include an FPGA or other programmable device that performs logic operations without processing computer-executable instructions. A processor device can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the disclosure herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A disease management system comprising:
a wearable device configured for placement on an individual's torso, the wearable device comprising:
a blood glucose sensor configured to measure blood glucose data;
a pose sensor configured to provide pose information of the individual;
a needle;
an actuator configured to administer glucagon to the individual; and
one or more processors in communication with the blood glucose sensor and the pose sensor and configured reduce a risk of the individual choking in response to administration of glucagon, the one or more processors programmed to:
determine a pose of the individual based at least in part on the pose information,
determine a blood glucose measurement based at least in part on the blood glucose data,
identify a hypoglycemic event of the individual based at least in part on the blood glucose measurement;
determine whether a status of the individual is a safe treatment status or an unsafe treatment status, wherein the safe treatment status is indicated by the detection of the hypoglycemic event and determination that the pose of the individual is a pose other than lying on their back, and wherein the unsafe treatment status is indicated by detection of the hypoglycemic event and determination that the pose of the individual is lying on their back;
cause, if the individual's status is the unsafe treatment status, at least one of an audible, visual, or vibratory alarm and revoke authorization for the actuator to administer glucagon, wherein the audible, visual, or vibratory alarm is indicative that the individual should reposition themself;
inject the needle into the individual, if the individual's status is the safe treatment status; and
administer, if the individual's status is the safe treatment status, the glucagon to the individual using the actuator via the needle.

2. The disease management system of claim 1, wherein the one or more processors are programmed to perform a calibration procedure, wherein performance of the calibration procedure calibrates the pose of the individual relative to a pose of the disease management system.

3. The disease management system of claim 2, wherein to perform the calibration procedure, the one or more processors are programmed to:
obtain a set of pose data from the pose sensor, wherein the set of pose data corresponds to a plurality of activities of the individual; and
calibrate the pose sensor based at least in part on the set of pose data.

4. The disease management system of claim 3, wherein the plurality of activities comprises standing, walking, running, sitting up, lying on back, lying on front, or lying on side.

5. The disease management system of claim 2, wherein to perform the calibration procedure, the one or more processors are programmed to:
obtain first pose information from the pose sensor, wherein the first pose information corresponds to a first activity of the individual;
obtain second pose information from the pose sensor, wherein the second pose information corresponds to a second activity of the individual; and
calibrate the pose sensor based at least in part on the first pose information and the first pose information.

6. The disease management system of claim 5, wherein the first activity correspond to standing and the second activity corresponds to walking in a straight line.

7. The disease management system of claim 5, wherein to obtain the first pose information, the one or more processors are programmed to:
communicate a first instruction indicating for the individual to perform the second activity,
determine that the individual is not moving, and
responsive to the determination that the individual is not moving, obtain the second pose information.

8. The disease management system of claim 5, wherein to obtain the second pose information, the one or more processors are programmed to:
communicate a second instruction indicating for the individual to perform the second activity,
determine that the individual is moving, and
responsive to the determination that the individual is moving, obtain the second pose information.

9. The disease management system of claim 1, wherein the one or more processors are programmed to confirm that the disease management system is coupled to the individual prior to causing administration of the glucagon to the individual.

10. The disease management system of claim 1, further comprising a sensor configured to measure conductance, wherein to determine confirm that the disease management system is coupled to the individual based at least on part on the measurement of the conductance.

11. The disease management system of claim 1, wherein the one or more processors are programmed to cause an alarm indicating to replace adhesive of the disease management system based at least in part on a determination that a conductance measurement does not satisfy a conductance threshold.

12. The disease management system of claim 1, wherein the one or more processors is programmed to determine a change in the individual's status from the unsafe treatment status to the safe treatment status in response to the audible, visual, or vibratory alarm and, restore authorization to administer glucagon to the actuator, and using the actuator, administer the glucagon to the individual while the individual's status is the safe treatment status.

13. A disease management system comprising:

a blood glucose sensor configured to measure blood glucose data;

a pose sensor configured for placement on an individual's torso and to provide pose information of the individual;

a needle;

an actuator configured to administer glucagon to the individual; and one or more processors in communication with the blood glucose sensor and the pose sensor and configured reduce a risk of the individual choking in response to administration of glucagon, the one or more processors programmed to:

determine a pose of the individual based at least in part on the pose information, determine a blood glucose measurement based at least in part on the blood glucose data, identify a hypoglycemic event of the individual based at least in part on the blood glucose measurement;

determine whether a status of the individual is a safe treatment status or an unsafe treatment status, wherein the safe treatment status is indicated by the detection of the hypoglycemic event and determination that the pose of the individual is lying on their back, and wherein the unsafe treatment status is indicated by detection of the hypoglycemic event and determination that the pose of the individual is a pose other than lying on their back;

cause, if the individual's status is the unsafe treatment status, at least one of an audible, visual, or vibratory alarm and revoke authorization for the actuator to administer glucagon, wherein the audible, visual, or vibratory alarm is indicative that the individual should reposition themself;

determine a change in the individual's status from the unsafe treatment status to the safe treatment status in response to the audible, visual, or vibratory alarm;

restore authorization to administer glucagon to the actuator in response to return to safe treatment status;

confirm that the disease management system is coupled to the individual prior to causing administration of the glucagon to the individual;

cause an alarm indicating to replace adhesive of the disease management system based at least in part on a determination that a conductance measurement does not satisfy a conductance threshold;

inject the needle into the individual while the individual's status is the safe treatment status; and administer, while the individual's status is the safe treatment status, the glucagon to the individual using the actuator via the needle.

14. The disease management system of claim 13, wherein the one or more processors are programmed to perform a calibration procedure, wherein performance of the calibration procedure calibrates the pose of the individual relative to a pose of the disease management system.

15. The disease management system of claim 14, wherein to perform the calibration procedure, the one or more processors are programmed to:

obtain a set of pose data from the pose sensor, wherein the set of pose data corresponds to a plurality of activities of the individual; and calibrate the pose sensor based at least in part on the set of pose data.

16. The disease management system of claim 15, wherein the plurality of activities comprises standing, walking, running, sitting up, lying on back, lying on front, or lying on side.

17. The disease management system of claim 14, wherein to perform the calibration procedure, the one or more processors are programmed to:

obtain first pose information from the pose sensor, wherein the first pose information corresponds to a first activity of the individual;

obtain second pose information from the pose sensor, wherein the second pose information corresponds to a second activity of the individual; and calibrate the pose sensor based at least in part on the first pose information and the first pose information.

18. The disease management system of claim 17, wherein the first activity correspond to standing and the second activity corresponds to walking in a straight line.

19. The disease management system of claim 17, wherein to obtain the first pose information, the one or more processors are programmed to:

communicate a first instruction indicating for the individual to perform the second activity, determine that the individual is not moving, and responsive to the determination that the individual is not moving, obtain the second pose information.

20. The disease management system of claim 17, wherein to obtain the second pose information, the one or more processors are programmed to:

communicate a second instruction indicating for the individual to perform the second activity, determine that the individual is moving, and responsive to the determination that the individual is moving, obtain the second pose information.

* * * * *